(12) United States Patent
Cannas et al.

(10) Patent No.: US 11,292,771 B2
(45) Date of Patent: Apr. 5, 2022

(54) AMIDINE CATALYST FOR CURABLE COMPOSITIONS

(71) Applicant: SIKA TECHNOLOGY AG, Baar (CH)

(72) Inventors: Rita Cannas, Dübendorf (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 16 days.

(21) Appl. No.: 16/843,379

(22) Filed: Apr. 8, 2020

(65) Prior Publication Data

US 2020/0231548 A1 Jul. 23, 2020

Related U.S. Application Data

(62) Division of application No. 15/580,967, filed as application No. PCT/EP2016/064303 on Jun. 21, 2016, now Pat. No. 10,647,681.

(30) Foreign Application Priority Data

Jun. 22, 2015 (EP) .................................... 15173193

(51) Int. Cl.
    *C07D 239/06* (2006.01)
    *C08G 77/38* (2006.01)
    *C09D 183/06* (2006.01)
    *C09J 183/06* (2006.01)

(52) U.S. Cl.
CPC ........... *C07D 239/06* (2013.01); *C08G 77/38* (2013.01); *C09D 183/06* (2013.01); *C09J 183/06* (2013.01)

(58) Field of Classification Search
CPC .. C07D 239/06; C07D 239/04; C07C 257/10; C08G 77/18; C08G 77/16; C08G 59/686; C08G 18/022; C08L 101/10; C08L 79/04
See application file for complete search history.

(56) References Cited

U.S. PATENT DOCUMENTS

| | | | |
|---|---|---|---|
| 2,743,241 A | 4/1956 | Groote | |
| 2,743,255 A | 4/1956 | Groote | |
| 2,994,685 A | 8/1961 | Delmonte et al. | |
| 3,949,076 A | 4/1976 | Bender et al. | |
| 5,364,955 A | 11/1994 | Zwiener et al. | |
| 7,985,424 B2 | 7/2011 | Tomalia et al. | |
| 8,063,161 B2 | 11/2011 | Dershem | |
| 2009/0029888 A1 | 1/2009 | Ravichandran et al. | |
| 2009/0281236 A1* | 11/2009 | Matsushita | C08L 101/10 524/588 |

FOREIGN PATENT DOCUMENTS

| | | |
|---|---|---|
| CN | 101747826 A | 6/2010 |
| FR | 2144724 A1 | 2/1973 |
| WO | 92-19601 A1 | 11/1992 |
| WO | 97/31033 A1 | 8/1997 |

OTHER PUBLICATIONS

USREGISTRY (Online), Columbus, Ohio (REGISTRY), 1222889-77-1, 165170-57-0, 802880-22-4, 204775-44-0, 63257-67-0, 882655-61-1, 27243-29-4, (May 13, 2010).
Jul. 30, 2020 Office Action issued in Chinese Patent Application 201680036334.1.
Mar. 15, 2021 Translation of Office Action issued in Chinese Application No. 201680036334.1.
USREGISTRY[Online], Columbus, Ohio, REGISTRY, 784103-99-7, 767594-14-9.
Lin et al. "Hydrothermal Synthesis and Charcterization of Two New Phosphatomolybdates(V) Containing Sanwich-Shaped [M(Mo6P4)2 Clusters (M=Co, Ni)" Journal of Cluster Science, vol. 19, No. 2, pp. 379-390, 2013.
V.I. et al. "Structure and tautomerism of substituted imidazolines." Zhurnal Priklkadnoi Khimii, vol. 41, No. 7, pp. 1585-1590, 1968.
Aug. 8, 2016 Search Report issued in International Patent Application No. PCT/EP2016/064303.
Dec. 26, 2017 International Preliminary Report on Patentability issued in International Patent Application No. PCT/EP2016/064303.
Jun. 26, 2019 Office Action issued in European Patent Application No. 16 733 369.9.

* cited by examiner

*Primary Examiner* — Kuo Liang Peng
(74) *Attorney, Agent, or Firm* — Oliff PLC

(57) ABSTRACT

The present invention relates to an amidine of the formula (I) and its use as a catalyst for crosslinking a curable composition. The amidine of the formula (I) contains at least one aliphatic amidine group. It is substantially odorless and nonvolatile at room temperature and accelerates the crosslinking of curable compositions very efficiently, without impairing the storage stability of the compositions. It is particularly suitable for compositions based on polymers containing silane groups, with which it is compatible, as a result of which such compositions do not have a tendency to separation or migration or evaporation of the catalyst.

15 Claims, No Drawings

AMIDINE CATALYST FOR CURABLE COMPOSITIONS

This is a Divisional of application Ser. No. 15/580,967 filed Dec. 8, 2017, which is a National Stage Application of PCT/EP2016/064303 filed Jun. 21, 2016, which in turn claims priority to European Application No. 15173193.2 filed Jun. 22, 2015. The entire disclosures of the prior applications are hereby incorporated by reference herein their entirety.

TECHNICAL FIELD

The invention relates to amidines and to the use thereof as catalysts for curable compositions.

STATE OF THE ART

Curable compositions play a significant role in many industrial applications, for example as adhesives, sealants or coatings. The curing thereof is brought about by crosslinking reactions which proceed via free or latent reactive groups, for example isocyanate groups, epoxide groups, hydroxyl groups, amino groups or silane groups, wherein these react with themselves or one another following a mixing operation or through heating or through contact with moisture, and hence bind the formation components present in the composition covalently to form a polymeric network. Acceleration of such crosslinking reactions is frequently accomplished using catalysts. These are very often substances of toxicological concern which constitute a potential hazard to users and the environment, especially after the curing of the composition, if the catalyst or degradation products thereof are released by outgassing, migration or washing-out.

Compositions curable at room temperature that are based on polymers containing silane groups are confronted with this problem to a significant degree. Polymers containing silane groups here are especially polyorganosiloxanes, which are commonly referred to as "silicones" or "silicone rubbers", and organic polymers containing silane groups, which are also referred to as "silane-functional polymers", "silane-modified polymers" (SMP) or "silane-terminated polymers" (STP). The crosslinking thereof proceeds via the condensation of silanol groups to form siloxane bonds and is conventionally catalyzed by means of organotin compounds such as dialkyltin(IV) carboxylates in particular. These are notable for very high activity in relation to the silanol condensation and are very hydrolysis-resistant, but they are harmful to health and a severe water pollution hazard. They are often combined with further catalysts, mainly basic compounds, such as amines in particular, which specifically accelerate the preceding hydrolysis of the silane groups.

Because greater weight is being given to EHS aspects by professional organizations and users and because of stricter government regulation, there have been increased efforts for some time to replace organotin compounds with other catalysts of lower toxicity. For instance, organotitanates, -zirconates and -aluminates have been described as alternative metal catalysts. However, these usually have lower catalytic activity in relation to the silanol condensation and bring about much slower crosslinking. Because of their lack of hydrolysis stability, they can lose a large part of their activity in the course of storage of the composition as a result of residual moisture in the ingredients, which causes the curing to slow significantly or stop entirely.

A further known alternative to organotin compounds is highly basic nitrogen compounds from the class of the amidines and guanidines, which can be used in combination with the metal catalysts mentioned or else alone. However, many of the commonly used amidine and guanidine catalysts, such as, in particular, 1,8-diazabicyclo[5.4.0]undec-7-ene (DBU) and 1,1,3,3-tetramethylguanidine (TMG), are volatile and odorous substances that are likewise harmful to health and hazardous to the environment. Moreover, they have a tendency to migrate because of low compatibility in the composition and hence to cause separation, exudation or substrate soiling. The described use of aromatic amidines and guanidines that are solid at room temperature provides a remedy here, but requires the use of suitable solvents and brings losses in catalytic activity and hence crosslinking rate.

SUMMARY OF THE INVENTION

It is therefore an object of the present invention to provide a catalyst for the crosslinking of curable compositions, especially compositions containing silane groups, which has a high catalytic activity for the crosslinking reaction and hence enables rapid curing of the composition applied, and also has a high selectivity for this crosslinking reaction and hence does not unduly impair the storage stability of the composition. Furthermore, the catalyst is to have a low vapor pressure and high compatibility with the composition, such that it has no tendency either to separate or migrate or to evaporate, and is to have minimum odor and low toxicity.

This object is achieved by an amidine of the formula (I) as described in claim 1. The amidine of the formula (I) contains at least one aliphatic amidine group. It has only low or zero volatility and exhibits high activity when used as a catalyst for curable compositions, whereas aromatic amidines have barely any or zero catalytic activity. By contrast with many catalysts having aliphatic amidine or guanidine groups that are known from the prior art, the amidine of the formula (I) is substantially odorless and nonvolatile at room temperature. It exhibits high catalytic activity coupled with good selectivity, especially in compositions based on polymers containing silane groups. This is particularly surprising, given that, on the basis of its relatively high molecular weight and the strong intermolecular interactions via hydrogen bonds, reduced activity would be expected as compared with smaller, less polar and hence more mobile amidines.

With these properties, the amidine of the formula (I) is particularly suitable for use in compositions based on polymers containing silane groups, where, as sole catalyst or in combination with further catalysts, it enables rapid curing to give a mechanically high-quality and durable material, without impairing the storability of the uncured composition. Both before and after curing, it has excellent compatibility with the composition and does not have any tendency either to separate or to migrate, by contrast with many similar compositions comprising amidine or guanidine catalysts according to the prior art, where catalyst-related migration effects play a major role. It enables low-emission and low-odor products which have neither greasy nor tacky surfaces, nor do they cause substrate soiling. Finally, the amidine of the formula (I) is preparable in a surprisingly simple process without auxiliaries from commercially available, inexpensive starting materials.

Further aspects of the invention are the subject of further independent claims. Particularly preferred embodiments of the invention are the subject of the dependent claims.

Ways of Executing the Invention

The invention provides an amidine of the formula (I)

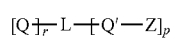   (I)

where p is an integer from 1 to 6 and r is an integer from 0 to 5, where (p+r) is an integer from 1 to 6, L is a (p+r)-valent hydrocarbyl radical having an average molecular weight in the range from 15 to 20,000 g/mol, optionally having heteroatoms, especially oxygen or nitrogen or silicon in the form of ether, tertiary amino, ester, amide, urethane, urea, uretdione, isocyanurate, biuret, allophanate, uretonimine, iminooxadiazinedione, oxadiazinetrione or alkoxysilane groups, or, in the case that r=0 and p=1, may also be a hydrogen radical, Q is a reactive group selected from glycidoxy, N-aziridinyl, (meth)acrylate, (meth)acrylamide, (meth)acrylonitrile, maleate, maleamide, maleimide, fumarate, fumaramide, itaconate, itaconamide, crotonate and crotonamide, Q' is a divalent connecting unit formed from the reaction of a reactive Q group with HZ, and Z is an aliphatic amidine group bonded via a nitrogen atom, where every Z is separated from every other Z by at least 2 carbon atoms, and where, in the case that r=0 and p=1 and of (meth)acrylamide or maleamide or fumaramide or itaconamide or crotonamide as reactive Q group, L and Q' may also together be a monovalent hydrocarbyl radical having 5 to 20 carbon atoms and having heteroatoms in the form of amide groups and optionally ether or ester groups.

In the present document, the term "aliphatic amidine group" refers to an amidine group which does not contain any nitrogen atom which is bonded directly to an aromatic ring or is part of a heteroaromatic ring system, for example imidazole or pyrimidine.

"Primary amino group" and "primary amine nitrogen" refer respectively to an $NH_2$ group and the nitrogen atom thereof that is bonded to an organic radical, and "secondary amino group" and "secondary amine nitrogen" refer respectively to an NH group and the nitrogen atom thereof that is bonded to two organic radicals which may also together be part of a ring, and "tertiary amino group" and "tertiary amine nitrogen" refer respectively to an N group and the nitrogen atom thereof that is bonded to three organic radicals, two or three of which together may also be part of one or more rings.

The term "silane group" refers to a silyl group which is bonded to an organic radical or to a polyorganosiloxane radical and has one to three, especially two or three, hydrolyzable substituents on the silicon atom. Particularly useful hydrolyzable substituents are alkoxy radicals. These silane groups are also referred to as "alkoxysilane groups". Silane groups may also be in partly or fully hydrolyzed form.

"Hydroxysilane", "isocyanatosilane", "aminosilane" and "mercaptosilane" refer respectively to organoalkoxysilanes having one or more hydroxyl, isocyanato, amino or mercapto groups on the organic radical in addition to the silane group.

Substance names beginning with "poly", such as polyol or polyisocyanate, refer to substances containing, in a formal sense, two or more of the functional groups that occur in their name per molecule.

The term "organic polymer" encompasses a collective of macromolecules that are chemically homogeneous but differ in relation to degree of polymerization, molar mass and chain length, which has been prepared by a poly reaction (polymerization, polyaddition, polycondensation) and has a majority of carbon atoms in the polymer backbone, and reaction products of such a collective of macromolecules. Polymers having a polyorganosiloxane backbone (commonly referred to as "silicones") are not organic polymers in the context of the present document.

The term "polyether containing silane groups" also encompasses organic polymers which contain silane groups and which, in addition to polyether units, may also contain urethane groups, urea groups or thiourethane groups. Such polyethers containing silane groups may also be referred to as "polyurethanes containing silane groups".

"Molecular weight" is understood in the present document to mean the molar mass (in grams per mole) of a molecule or part of a molecule, also referred to as "radical". "Average molecular weight" is understood to mean the number-average $M_n$ of an oligomeric or polymeric mixture of molecules or radicals, which is typically determined by means of gel permeation chromatography (GPC) against polystyrene as standard.

"Storage-stable" or "storable" refers to a substance or composition when it can be stored at room temperature in a suitable container over a prolonged period, typically at least 3 months up to 6 months or more, without any change in its application or use properties, especially in the viscosity and crosslinking rate, to a degree of relevance for the use thereof as a result of the storage.

A dotted line in the formulae in this document in each case represents the bond between a substituent and the corresponding molecular radical.

"Room temperature" refers to a temperature of about 23° C.

Preferably, Z is

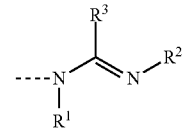

where $R^1$ where $R^1$ is a hydrogen radical or an alkyl or cycloalkyl or aralkyl radical having 1 to 8 carbon atoms or together with $R^2$ is $R^4$, $R^2$ is a hydrogen radical or an alkyl, cycloalkyl or aralkyl radical which has 1 to 18 carbon atoms and optionally contains ether oxygen or tertiary amine nitrogen, or together with $R^1$ is $R^4$, $R^3$ is a hydrogen radical or an alkyl or cycloalkyl or aralkyl radical having 1 to 12 carbon atoms, where $R^4$ is an optionally substituted 1,2-ethylene, 1,3-propylene or 1,4-butylene radical having 2 to 12 carbon atoms, and where $R^2$ and $R^3$ together may also be an alkylene radical having 3 to 6 carbon atoms.

$R^1$ is preferably an alkyl or cycloalkyl or aralkyl radical having 1 to 4 carbon atoms or together with $R^2$ is $R^4$.

$R^2$ is preferably an alkyl, cycloalkyl or aralkyl radical which has 1 to 12, especially 1 to 8, carbon atoms and optionally contains ether oxygen or tertiary amine nitrogen, or together with $R^1$ is $R^4$.

$R^3$ is preferably a hydrogen radical or an alkyl, cycloalkyl or aralkyl radical having 1 to 8, especially 1 to 4, carbon atoms.

$R^3$ is more preferably a hydrogen radical or methyl radical, most preferably a methyl radical.

More preferably, $R^1$ and $R^2$ together are $R^4$.

More preferably, Z thus has the formula

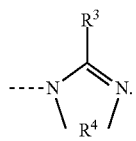

Such an amidine of the formula (I) is preparable in a particularly simple manner and in high purity.

$R^4$ preferably has 2 to 6 carbon atoms.

$R^4$ is preferably 1,2-ethylene, 1,2-propylene, 1,3-propylene, 2-methyl-1,2-propylene, 2,2-dimethyl-1,3-propylene, 1,3-butylene, 1,4-butylene, 1,3-pentylene, 1,2-cyclohexylene, 1,3-cyclohexylene or 2(4)-methyl-1,3-cyclohexylene.

$R^4$ is more preferably 1,2-ethylene, 1,2-propylene, 1,3-propylene, 2-methyl-1,2-propylene, 2,2-dimethyl-1,3-propylene, 1,3-butylene or 1,3-pentylene, especially 1,2-ethylene or 1,3-propylene.

Most preferably, $R^4$ is 1,3-propylene.

More preferably, $R^3$ is methyl and $R^4$ is 1,3-propylene. Such an amidine has particularly high catalytic activity and is preparable in a particularly simple manner.

p is preferably 1 or 2 or 3.

r is preferably 0.

(p+r) is preferably 1 or 2 or 3.

More preferably, p is 1 or 2 or 3 and r is 0.

L is preferably a (p+r)-valent hydrocarbyl radical which has an average molecular weight in the range from 15 to 5,000 g/mol, especially 15 to 2,000 g/mol, and optionally contains oxygen or nitrogen or silicon in the form of ether, tertiary amino, ester, urethane, isocyanurate, biuret, allophanate or alkoxysilane groups, or is a hydrogen radical.

If Q is glycidoxy or N-aziridinyl, L is preferably not a hydrogen radical. Such an amidine of the formula (I) is free of primary hydroxyl groups and free of primary amino groups and hence is particularly storage-stable together with silane groups and/or isocyanate groups.

Q is preferably a reactive group selected from glycidoxy, N-aziridinyl, (meth)acrylate, (meth)acrylamide, maleate, maleamide, maleimide and itaconate.

Glycidoxy is a reactive group of the formula

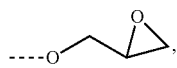

N-aziridinyl is a reactive group of the formula

(meth)acrylate or (meth)acrylamide or itaconate is a reactive group of the formula

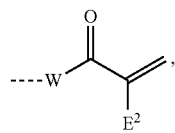

maleate or maleamide is a reactive group of the formula

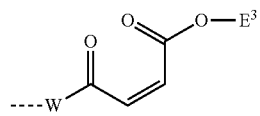

and maleimide is a reactive group of the formula

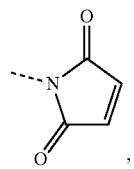

where

W is O or $NR^5$, where $R^5$ is a hydrogen radical or a monovalent hydrocarbyl radical having 1 to 8 carbon atoms or together with L is an optionally substituted alkylene radical which has 2 to 6 carbon atoms and optionally contains an ether oxygen, $E^1$ is a hydrogen radical or methyl radical, $E^2$ is a hydrogen radical or methyl radical or alkoxycarbonylmethyl radical having 3 to 10 carbon atoms, and $E^3$ is an alkyl radical having 1 to 8 carbon atoms.

$R^5$ is preferably methyl, ethyl, propyl, isopropyl, butyl, tert-butyl or together with L is 3-oxa-1,5-pentylene.

W is preferably O.

$E^2$ is preferably a hydrogen radical or a methyl, methoxycarbonylmethyl, ethoxycarbonylmethyl or butoxycarbonylmethyl radical, especially a hydrogen radical or a methyl radical.

$E^3$ is preferably methyl, ethyl or a butyl radical.

Q' is preferably selected from the group consisting of

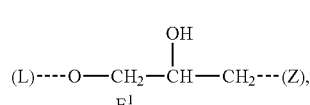

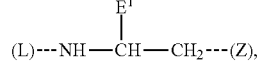

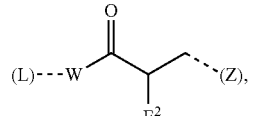

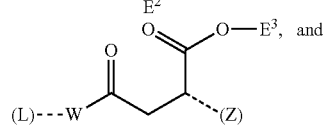

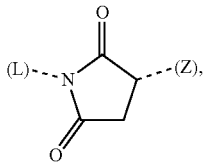

where W, $E^1$, $E^2$ and $E^3$ have the definitions already given.

The letters (L) and (Z) between brackets represent the bond from Q' to L and Z respectively.

If Q' is

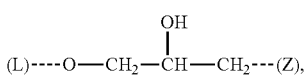

Q' has formed from the reaction of HZ with a glycidoxy group.

L in this case is preferably a (p+r)-valent hydrocarbyl radical which has a molecular weight in the range from 15 to 1,500 g/mol and optionally contains ether oxygens and optionally an alkoxysilane group, more preferably a radical selected from the group consisting of 2-ethylhexyl glycidyl ether, $C_8$- to $C_{10}$-alkyl glycidyl ether, $C_{12}$- to $C_{14}$-alkyl glycidyl ether, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having an average molecular weight in the range from 280 to 1,500 g/mol, bisphenol A diglycidyl ether, bisphenol F diglycidyl ether, 3-glycidoxypropyltrimethoxysilane and 3-glycidoxypropyltriethoxysilane, in each case after removal of the glycidoxy groups.

More preferably in this case, p is 1 and r is 0 and L is triethoxysilylpropyl or trimethoxysilylpropyl. Such an amidine of the formula (I) is particularly suitable as catalyst for compositions containing silane groups, where it can be covalently bonded via the silane groups in the course of curing.

If Q' is

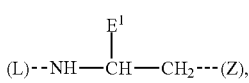

Q' has formed from the reaction of HZ with an N-aziridinyl group.

L in this case is preferably a (p+r)-valent hydrocarbyl radical which has an average molecular weight in the range from 15 to 2,000 g/mol, especially 87 to 500 g/mol, and especially has oxygen in the form of ester groups.

If Q' is

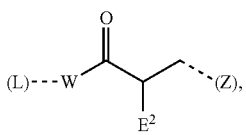

Q' has formed from the reaction of HZ with a (meth)acrylate or (meth)acrylamide or itaconate or itaconamide group.

L in this case is preferably a (p+r)-valent hydrocarbyl radical which has an average molecular weight in the range from 15 to 5,000 g/mol, especially 15 to 2,000 g/mol, and optionally has oxygen or nitrogen or silicon in the form of ether, tertiary amino, ester, urethane, isocyanurate, biuret, allophanate and/or alkoxysilane groups, especially a radical selected from the group consisting of butyl, 2-ethylhexyl, trimethoxysilylpropyl, triethoxysilylpropyl, 1,2-ethylene, 3,6,9-trioxa-1,11-undecylene, 2,5-dimethyl-3,6-dioxa-1,8-nonylene, a polyoxyethylene radical having a molecular weight in the range from 200 to 2,000 g/mol, a polyoxypropylene radical having a molecular weight in the range from 200 to 2,000 g/mol, 1,4-butylene, 1,6-hexylene, 2,2-dimethyl-1,3-propylene, trimethylolpropane after removal of the three hydroxyl groups, and polyurethane polymers having (meth)acrylate groups and having an average molecular weight in the range from 500 to 5,000 g/mol, especially 500 to 2,000 g/mol, especially from the reaction of 2-hydroxyethyl acrylate with polyurethane polymers containing isocyanate groups.

More preferably in this case, p is 1 and r is 0 and L is triethoxysilylpropyl or trimethoxysilylpropyl. Such an amidine of the formula (I) is particularly suitable as catalyst for compositions containing silane groups, where it can be covalently bonded via the silane groups in the course of curing.

If W is $NR^5$, L is also preferably, together with $R^5$, an optionally substituted alkylene radical which has 2 to 6 carbon atoms and optionally contains an ether oxygen.

If Q' is

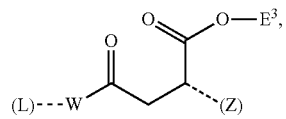

Q' has formed from the reaction of HZ with a maleate or maleamide or fumarate or fumaramide group.

L in this case is preferably a monovalent hydrocarbyl radical having 1 to 8 carbon atoms, especially methyl or ethyl and butyl.

If Q' is

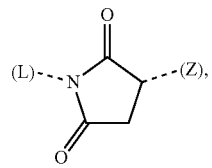

Q' has formed from the reaction of HZ with a maleimide group.

L in this case is preferably a hydrogen radical or a mono- or divalent hydrocarbyl radical having 1 to 12 carbon atoms, especially a hydrogen radical or methyl, ethyl, butyl or hexyl, or 1,2-ethylene or 1,4-butylene or 1,6-hexylene.

The preferred amidines of the formula (I) are preparable from readily obtainable starting materials in a simple process and/or have particularly high catalytic activity.

The amidine of the formula (I) may also be in tautomeric form. All possible tautomeric forms of the amidines are considered to be equivalent in the context of the present invention.

In addition, the amidine of the formula (I) may be in protonated form.

The amidine of the formula (I) may likewise be in complexed form, especially with cations of zinc, iron or molybdenum.

One example of the case that L and Q' together are a (p+r)-valent hydrocarbyl radical which has 5 to 20 carbon atoms and has heteroatoms in the form of amide groups and optionally ether or ester groups is the reaction product shown in the formula below, formed from a cyclic amidine HZ and 4-acryloylmorpholine.

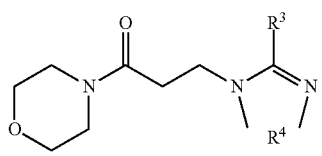

In a preferred embodiment of the invention, the amidine of the formula (I) is free of hydroxyl groups. In this case, Q is especially selected from (meth)acrylate, (meth)acrylamide, (meth)acrylonitrile, maleate, maleamide, maleimide, fumarate, fumaramide, itaconate, itaconamide, crotonate and crotonamide, especially (meth)acrylate. Such an amidine of the formula (I) is particularly storage-stable together with silane groups and/or isocyanate groups. It is particularly suitable as a catalyst for compositions containing silane groups or containing isocyanate groups.

In a further preferred embodiment of the invention, the amidine of the formula (I) contains a silane group. In this case, more particularly, p is 1, r is 0, L is an alkylene radical which is substituted by an alkoxysilane group and has 1 to 6 carbon atoms, and Q' is

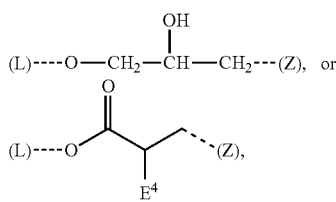

where $E^4$ is a hydrogen radical or methyl radical. Such an amidine of the formula (I) is particularly suitable as catalyst for compositions containing silane groups, where it can be covalently bonded via the silane groups in the course of curing. It is especially derived from a glycidoxy-functional or a (meth)acryloyloxy-functional organosilane.

The amidine especially has the formula (I') or the formula (I″)

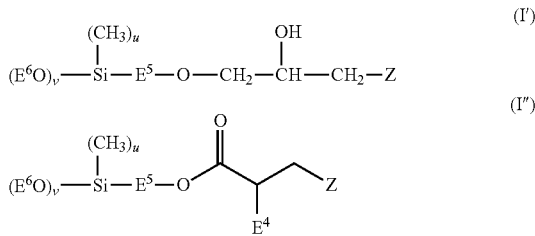

where
$E^4$ is a hydrogen radical or methyl radical,
$E^5$ is an alkylene radical having 1 to 6 carbon atoms, especially 1,3-propylene,
$E^6$ is an alkyl radical having 1 to 4 carbon atoms, especially methyl or ethyl, and
u is 0 or 1 and v is 2 or 3, where (u+v) is 3.

The amidine of the formula (I) is preferably obtained by the reaction of
at least one amidine of the formula HZ
with
at least one functional compound of the formula L—[Q]$_{(p+r)}$,
where
L is
a (p+r)-valent hydrocarbyl radical having an average molecular weight in the range from 15 to 20,000 g/mol, optionally having heteroatoms, especially oxygen or nitrogen or silicon in the form of ether, tertiary amino, ester, amide, urethane, urea, uretdione, isocyanurate, biuret, allophanate, uretonimine, iminooxadiazinedione, oxadiazinetrione or alkoxysilane groups, or, in the case that r=0 and p=1, may also be a hydrogen radical, or, in the case that r=0 and p=1 and of (meth)acrylamide or maleamide or fumaramide or itaconamide or crotonamide as reactive Q group, L and Q may also together be a monovalent hydrocarbyl radical having 5 to 20 carbon atoms and having heteroatoms in the form of amide groups and optionally ether or ester groups,
and Z, Q, p and r have the definitions already given.

Preferably, L is a (p+r)-valent hydrocarbyl radical which has an average molecular weight in the range from 15 to 5,000 g/mol, especially 15 to 2,000 g/mol, and optionally contains oxygen or nitrogen or silicon in the form of ether, tertiary amino, ester, urethane, isocyanurate, biuret, allophanate or alkoxysilane groups, or is a hydrogen radical.

If Q is glycidoxy or N-aziridinyl, L is preferably not a hydrogen radical. Such an amidine of the formula (I) is free of primary hydroxyl groups and free of primary amino groups and hence is particularly storage-stable together with silane groups and/or isocyanate groups.

If Q is a glycidoxy group, L is preferably a (p+r)-valent hydrocarbyl radical which has a molecular weight in the range from 15 to 1,500 g/mol and optionally contains ether oxygens and optionally an alkoxysilane group, more preferably a radical selected from the group consisting of 2-ethylhexyl glycidyl ether, $C_8$- to $C_{10}$-alkyl glycidyl ether, $C_{12}$- to $C_{14}$-alkyl glycidyl ether, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having an average molecular weight in the range from 280 to 1,500 g/mol, bisphenol A diglycidyl ether, bisphenol F diglycidyl ether, 3-glycidoxypropyltrimethoxysilane and 3-glycidoxypropyltriethoxysilane, in each case after removal of the glycidoxy groups.

More preferably in this case, p is 1 and r is 0 and L is triethoxysilylpropyl or trimethoxysilylpropyl. Such an amidine of the formula (I) is particularly suitable as catalyst for compositions containing silane groups, where it can be covalently bonded via the silane groups in the course of curing.

If Q is an N-aziridinyl group, L is preferably a (p+r)-valent hydrocarbyl radical which has an average molecular weight in the range from 15 to 2,000 g/mol, especially 87 to 500 g/mol, and especially has oxygen in the form of ester groups.

If Q is a (meth)acrylate or (meth)acrylamide or itaconate or itaconamide group, L is preferably a (p+r)-valent hydrocarbyl radical which has an average molecular weight in the range from 15 to 5,000 g/mol, especially 15 to 2,000 g/mol, and optionally has oxygen or nitrogen or silicon in the form of ether, tertiary amino, ester, urethane, isocyanurate, biuret, allophanate and/or alkoxysilane groups, especially a radical selected from the group consisting of butyl, 2-ethylhexyl, trimethoxysilylpropyl, triethoxysilylpropyl, 1,2-ethylene, 3,6,9-trioxa-1,11-undecylene, 2,5-dimethyl-3,6-dioxa-1,8-nonylene, a polyoxyethylene radical having a molecular weight in the range from 200 to 2,000 g/mol, a polyoxypropylene radical having a molecular weight in the range from 200 to 2,000 g/mol, 1,4-butylene, 1,6-hexylene, 2,2-dimethyl-1,3-propylene, trimethylolpropane after removal of the three hydroxyl groups, and polyurethane polymers having (meth)acrylate groups and having an average molecular weight in the range from 500 to 5,000 g/mol, especially 500 to 2,000 g/mol, especially from the reaction of 2-hydroxyethyl acrylate with polyurethane polymers containing isocyanate groups.

More preferably, p is 1 and r is 0 and L is triethoxysilylpropyl or trimethoxysilylpropyl. Such an amidine of the formula (I) is particularly suitable as catalyst for compositions containing silane groups, where it can be covalently bonded via the silane groups in the course of curing.

If Q is a maleate or maleamide or fumarate or fumaramide group, L is preferably a monovalent hydrocarbyl radical having 1 to 8 carbon atoms, especially methyl or ethyl or butyl.

If Q is a maleimide group, L is preferably a hydrogen radical or a mono- or divalent hydrocarbyl radical having 1 to 12 carbon atoms, especially a hydrogen radical or methyl, ethyl, butyl or hexyl, or 1,2-ethylene or 1,4-butylene or 1,6-hexylene.

The reaction of the amidine of the formula HZ with the functional compound of the formula L―[Q]$_{(p+r)}$ is especially effected under conditions as typically used for reactions between the reactive groups involved in the particular reaction, preferably at a temperature in the range from 20 to 160° C., especially to 140° C. The reaction can be effected with use of a solvent or preferably in a solvent-free manner. It is optionally possible to also use auxiliaries, for example catalysts, initiators or stabilizers. Preferably, no solvents and auxiliaries are used in the reaction.

The amidine of the formula HZ is preferably used in a roughly stoichiometric or slightly superstoichiometric amount in relation to the reactive groups of the functional compound. This reaction is preferably conducted such that all the reactive groups of the functional compound are converted.

The reaction product from this reaction is preferably used, without workup or purification, as catalyst for the crosslinking of a curable composition. The reaction product here may contain proportions of by-products or unconverted starting materials.

The invention thus further provides a process for preparing the amidine of the formula (I), wherein at least one amidine of the formula HZ is reacted with at least one functional compound of the formula L―[Q]$_{(p+r)}$, as described above.

If the functional compound of the formula L―[Q]$_{(p+r)}$ has more than one reactive group, these are preferably the same, as, for example, in diglycidyls or triacrylates. Alternatively, it is possible that the functional compound has various reactive groups.

Suitable functional compounds of the formula L―[Q]$_{(p+r)}$ are especially commercially available substances.

Preferred functional compounds of the formula L―[Q]$_{(p+r)}$ are glycidyl ethers or glycidyl esters, especially aliphatic glycidyl ethers, preferably allyl glycidyl ether, butyl glycidyl ether, hexyl glycidyl ether, 2-ethylhexyl glycidyl ether, glycidyl ethers of fatty alcohols, such as, in particular, $C_8$- to $C_{10}$-alkyl glycidyl ethers or $C_{12}$- to $C_{14}$-alkyl glycidyl ethers, epoxysilanes such as, in particular, 3-glycidoxypropyltrimethoxysilane, 3-glycidoxypropyltriethoxysilane, 3-glycidoxypropyldimethoxymethylsilane or 3-glycidoxypropyldiethoxymethylsilane, glycidyl ethers of phenol, cresol, tert-butylphenol or cardanol, or aliphatic polyglycidyl ethers, preferably glycidyl ethers of ethylene glycol, propylene glycol, butylene glycol, hexanediol, octanediol, polypropylene glycols, dimethylolcyclohexane, neopentyl glycol, castor oil, trimethylolpropane, trimethylolethane, pentaerythritol, glycerol, alkoxylated glycerol or alkoxylated trimethylolpropane, or ring-hydrogenated bisphenol A, F or A/F liquid resins; or aromatic polyglycidyl ethers, preferably glycidyl ethers of bisphenol A, bisphenol F or bisphenol A/F, or novolak glycidyl ethers, especially in the form of what are called liquid resins, as are commercially available, for example, from Dow, Huntsman or Hexion;

N-alkylaziridines, especially Michael adducts of aziridine or 2-methylaziridine, preferably methyl 3-(aziridin-1-yl)propanoate, methyl 3-(2-methylaziridin-1-yl)-propanoate, butyl 3-(aziridin-1-yl)propanoate, butyl 3-(2-methylaziridin-1-yl)-propanoate, 1,1,1-trimethylolpropane tris(3-(aziridin-1-yl)-propanoate), 1,1,1-trimethylolpropane tris(3-(2-methylaziridin-1-yl) propanoate), pentaerythritol tetrakis (3-(aziridin-1-yl) propanoate or pentaerythritol tetrakis(3-(2-methylaziridin-1-yl)propanoate);

(meth)acrylates, especially acrylates or methacrylates, preferably methyl (meth)acrylate, ethyl (meth)acrylate, butyl (meth)acrylate, tert-butyl (meth)acrylate, 2-ethylhexyl (meth)acrylate, lauryl (meth)acrylate, stearyl (meth)acrylate, cyclohexyl (meth)acrylate, tetrahydrofuryl (meth)acrylate, isobornyl (meth)acrylate, 2-phenoxyethyl (meth)acrylate, 2-(2-phenoxyethoxy)ethyl (meth)acrylate, 2-(4-nonylphenoxy)ethyl (meth)acrylate, 3-(meth)acryloyloxypropyltrimethoxysilane, 3-(meth)acryloyloxypropyltriethoxysilane, 3-(meth) acryloyloxypropyldimethoxymethylsilane or 3-(meth) acryloyloxypropyldiethoxymethylsilane; di- or polyfunctional acrylates or methacrylates of polyethers, polyesters, novolaks, phenols, aliphatic or cycloaliphatic alcohols, glycols, polyester glycols or mono- or polyalkoxylated derivatives of the aforementioned compounds, preferably ethylene glycol di(meth) acrylate, tetraethylene glycol di(meth)acrylate, tripropylene glycol di(meth)acrylate, polyethylene glycol di(meth)acrylate, polypropylene glycol di(meth)acrylate, butane-1,4-diol di(meth)acrylate, hexane-1,6-diol di(meth)acrylate, neopentyl glycol di(meth)acrylate, trimethylolpropane tri(meth)acrylate, pentaerythritol tetra(meth)acrylate, dipentaerythritol tetra(meth)acrylate, dipentaerythritol penta(meth)acrylate, dipentaerythritol hexa(meth)acrylate; di- or poly-acryloyl- or -methacryloyl-functional polybutadienes, polyisoprenes or block copolymers thereof; adducts of di- or polyfunctional glycidyl ethers or glycidyl esters, such as those with acrylic acid and methacrylic acid that have already been mentioned; di- or polyfunctional polyurethane (meth)acrylates, especially reaction products of polyurethane polymers containing isocyanate groups with 2-hydroxyethyl acrylate; or tris(2-hydroxyethyl) isocyanurate tri(meth)acrylate or tris(2-hydroxyethyl) cyanurate tri(meth)acrylate;

(meth)acrylamides, especially acrylamide, methacrylamide or N-substituted acrylamides or methacrylamides, preferably N,N-dimethylacrylamide, N,N-diethylacrylamide,N-methylacrylamide, N-ethylacrylamide, N-propylacrylamide, N-isopropylacrylamide, N-butylacrylamide, N-tert-butylacrylamide, N,N-dimethylaminopropylacrylamide, N-butoxymethylacrylamide or N-isobutoxymethylacrylamide; or di- or polyfunctional acrylamides or methacrylamides, preferably N,N'-methylenebis(acrylamide), N,N'-ethylenebis(acrylamide) or N,N',N"-tris((meth)acryloyl)perhydrotriazine, or cyclic (meth)acrylamides, especially 4-acryloylmorpholine;

maleates, especially dialkyl maleates, preferably dimethyl maleate, diethyl maleate or dibutyl maleate;

maleimides, especially maleimide or N-alkylmaleimides, preferably N-methylmaleimide, N-ethylmaleimide, N-butylmaleimide, N-hexylmaleimide or 1,1-(1,6-hexylene)bis(1H-pyrrole-2,5-dione);

itaconates, especially dialkyl itaconates, preferably dimethyl itaconate, diethyl itaconate, dibutyl itaconate or dihexyl itaconate.

More preferably, the functional compound of the formula L—[Q]$_{(p+r)}$ is selected from the group consisting of 2-ethylhexyl glycidyl ether, $C_8$- to $C_{10}$-alkyl glycidyl ether, $C_{12}$- to $C_{14}$-alkyl glycidyl ether, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having an average molecular weight in the range from 280 to 1,000 g/mol, bisphenol A diglycidyl ether, bisphenol F diglycidyl ether, 3-glycidoxypropyltrimethoxysilane, 3-glycidoxypropyltriethoxysilane, butyl (meth)acrylate, tert-butyl (meth)acrylate, 2-ethylhexyl (meth)acrylate, (meth)acryloyloxypropyltrimethoxysilane, (meth)acryloyloxypropyltriethoxysilane, ethylene glycol di(meth)acrylate, tetraethylene glycol di(meth)acrylate, tripropylene glycol di(meth)acrylate, polyethylene glycol di(meth)acrylate having an average molecular weight in the range from 200 to 2,000 g/mol, polypropylene glycol di(meth)acrylate having an average molecular weight in the range from 200 to 2,000 g/mol, butane-1,4-diol di(meth)acrylate, hexane-1,6-diol di(meth)acrylate, neopentyl glycol di(meth)acrylate, trimethylolpropane tri(meth)acrylate, di- or polyfunctional polyurethane (meth)acrylates having an average molecular weight in the range from 500 to 5,000 g/mol from the reaction of polyurethane polymers containing isocyanate groups with 2-hydroxyethyl acrylate, 4-acryloylmorpholine, acrylonitrile, diethyl maleate, diethyl fumarate, N-ethylmaleimide and diethyl itaconate.

In a preferred embodiment of the invention, the amidine of the formula (I) is free of hydroxyl groups. More preferably, the functional compound of the formula L—[Q]$_{(p+r)}$ is selected from the group consisting of butyl (meth)acrylate, tert-butyl (meth)acrylate, 2-ethylhexyl (meth)acrylate, (meth)acryloyloxypropyltrimethoxysilane, (meth)acryloyloxypropyltriethoxysilane, ethylene glycol di(meth)acrylate, tetraethylene glycol di(meth)acrylate, tripropylene glycol di(meth)acrylate, polyethylene glycol di(meth)acrylate having an average molecular weight in the range from 200 to 2,000 g/mol, polypropylene glycol di(meth)acrylate having an average molecular weight in the range from 200 to 2,000 g/mol, butane-1,4-diol di(meth)acrylate, hexane-1,6-diol di(meth)acrylate, neopentyl glycol di(meth)acrylate, trimethylolpropane tri(meth)acrylate, di- or polyfunctional polyurethane (meth)acrylates having an average molecular weight in the range from 500 to 5,000 g/mol from the reaction of polyurethane polymers containing isocyanate groups with 2-hydroxyethyl acrylate, 4-acryloylmorpholine, acrylonitrile, diethyl maleate, diethyl fumarate, N-ethylmaleimide and diethyl itaconate.

In a further preferred embodiment of the invention, the amidine of the formula (I) contains a silane group and especially has the formula (I') or the formula (I").

This functional compound of the formula L—[Q]$_{(p+r)}$ is especially selected from the group consisting of 3-glycidoxypropyltrimethoxysilane, 3-glycidoxypropyltriethoxysilane, (meth)acryloyloxypropyltrimethoxysilane and (meth)acryloyloxypropyltriethoxysilane.

The amidine of the formula HZ especially has the formula

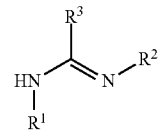

where $R^1$, $R^2$ and $R^3$ have the definitions already given.

A preferred amidine of the formula HZ is a cyclic amidine of the formula

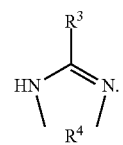

Such a cyclic amidine is preparable in a particularly simple manner.

The cyclic amidine of the formula HZ is preferably selected from the group consisting of imidazoline, 2-methylimidazoline, 4(5)-methylimidazoline, 2,4(5)-dimethylimidazoline, 4,4(5,5)-dimethylimidazoline, 2,4,4(2,5,5)-trimethylimidazoline, 1,4,5,6-tetrahydropyrimidine, 2-methyl-1,4,5,6-tetrahydropyrimidine, 5,5-dimethyl-1,4,5,6-tetrahydropyrimidine, 2,5,5-trimethyl-1,4,5,6-tetrahydropyrimidine, 4(6)-methyl-1,4,5,6-tetrahydropyrimidine, 2,4(2,6)-dimethyl-1,4,5,6-tetrahydropyrimidine, 4(6)-ethyl-1,4,5,6-tetrahydropyrimidine and 4(6)-ethyl-2-methyl-1,4,5,6-tetrahydropyrimidine. Among these, preference is given to imidazoline, 2-methylimidazoline, 1,4,5,6-tetrahydropyrimidine or 2-methyl-1,4,5,6-tetrahydropyrimidine.

Most preferred is 2-methyl-1,4,5,6-tetrahydropyrimidine.

An especially preferred amidine of the formula (I) is one which has been obtained from the reaction of 2-methyl-1,4,5,6-tetrahydropyrimidine with a functional compound selected from the group consisting of 2-ethylhexyl glycidyl ether, $C_8$- to $C_{10}$-alkyl glycidyl ether, $C_{12}$- to $C_{14}$-alkyl glycidyl ether, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having an average molecular weight in the range from 280 to 1,000 g/mol, bisphenol A diglycidyl ether, bisphenol F diglycidyl ether, 3-glycidoxypropyltrimethoxysilane, 3-glycidoxypropyltriethoxysilane, butyl (meth)acrylate, tert-butyl (meth)acrylate, 2-ethylhexyl (meth)acrylate, (meth)acryloyloxypropyltrimethoxysilane, (meth)acryloyloxypropyltriethoxysilane, ethylene glycol di(meth)acrylate, tetraethylene glycol di(meth)acrylate, tripropylene glycol di(meth)acrylate, polyethylene glycol di(meth)acrylate having an average molecular weight in the range from 200 to 2,000 g/mol, polypropylene glycol di(meth)acrylate having an average molecular weight in the range from 200 to 2,000 g/mol, butane-1,4-diol di(meth)acrylate, hexane-1,6-diol di(meth)acrylate, neopentyl glycol di(meth)acrylate, trimethylolpropane tri(meth)acrylate, di- or polyfunctional polyurethane (meth)acrylates having an average molecular weight in the range from 500 to 5,000 g/mol from the reaction of polyurethane polymers containing isocyanate groups with 2-hydroxyethyl acrylate, 4-acryloylmorpholine, acrylonitrile, diethyl maleate, diethyl fumarate, N-ethylmaleimide and diethyl itaconate.

A very particularly preferred amidine of the formula (I) is one which is free of hydroxyl groups and has been obtained from the reaction of 2-methyl-1,4,5,6-tetrahydropyrimidine with a functional compound selected from the group consisting of butyl (meth)acrylate, tert-butyl (meth)acrylate, 2-ethylhexyl (meth)acrylate, (meth)acryloyloxypropyltrimethoxysilane, (meth)acryloyloxypropyltriethoxysilane, ethylene glycol di(meth)acrylate, tetraethylene glycol di(meth)acrylate, tripropylene glycol di(meth)acrylate, polyethylene glycol di(meth)acrylate having an average molecular weight in the range from 200 to 2,000 g/mol, polypropylene glycol di(meth)acrylate having an average molecular weight in the range from 200 to 2,000 g/mol, butane-1,4-diol di(meth)acrylate, hexane-1,6-diol di(meth)acrylate, neopentyl glycol di(meth)acrylate, trimethylolpropane tri(meth)acrylate, di- or polyfunctional polyurethane (meth)acrylates having an average molecular weight in the range from 500 to 5,000 g/mol from the reaction of polyurethane polymers containing isocyanate groups with 2-hydroxyethyl acrylate, 4-acryloylmorpholine, acrylonitrile, diethyl maleate, diethyl fumarate, N-ethylmaleimide and diethyl itaconate.

Very particular preference is further given to an amidine of the formula (I) which contains a silane group and has the formula (I') or the formula (I") and has been obtained from the reaction of 2-methyl-1,4,5,6-tetrahydropyrimidine with a functional compound selected from the group consisting of 3-glycidoxypropyltrimethoxysilane, 3-glycidoxypropyltriethoxysilane, (meth)acryloyloxypropyltrimethoxysilane and (meth)acryloyloxypropyltriethoxysilane.

A cyclic amidine of the formula

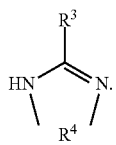

is for its part especially obtained from the reaction of at least one diamine of the formula $NH_2$—$R^4$—$NH_2$ with at least one reagent for introduction of amidine groups.

The reaction product from this reaction can be used without further workup for preparation of an amidine of the formula (I).

A suitable diamine of the formula $NH_2$—$R^4$—$NH_2$ is especially ethylenediamine, propane-1,2-diamine, propane-1,3-diamine, 2-methylpropane-1,2-diamine, 2,2-dimethylpropane-1,3-diamine, butane-1,3-diamine, butane-1,4-diamine, pentane-1,3-diamine (DAMP), 1,2-diaminocyclohexane, 1,3-diaminocyclohexane or 2(4)-methyl-1,3-diaminocyclohexane. Preference is given to ethylenediamine, propane-1,2-diamine, propane-1,3-diamine, 2-methylpropane-1,2-diamine, 2,2-dimethylpropane-1,3-diamine, butane-1,3-diamine or pentane-1,3-diamine (DAMP). Particular preference is given to ethylenediamine or propane-1,3-diamine.

Most preferred is propane-1,3-diamine.

The reagent for introduction of amidine groups is preferably selected from the group consisting of ortho esters, 1,3-keto esters, 1,3-keto amides, nitriles, imido esters, imidoyl chlorides, amide and lactams.

Among these, preference is given to ortho esters, 1,3-keto esters or nitriles. Preferred ortho esters are ortho esters of the formula $R^3$—$C(OR^6)_3$ where $R^6$ is an alkyl radical having 1 to 4 carbon atoms and $R^3$ has the definitions already given, especially an orthoformate, orthoacetate, orthopropionate, orthobutyrate or orthovalerate, more preferably trimethyl orthoformate, triethyl orthoformate, trimethyl orthoacetate or triethyl orthoacetate.

Preferred 1,3-keto esters are 1,3-keto esters of the formula $R^3$—$C(O)CH_2C(O)OR^6$ where $R^6$ and $R^3$ have the definitions already given, especially methyl acetoacetate, ethyl acetoacetate, isopropyl acetoacetate or tert-butyl acetoacetate, more preferably ethyl acetoacetate.

Preferred nitriles are nitriles of the formula $R^3$—CN where $R^3$ has the definitions already given, especially acetonitrile, propionitrile, butyronitrile, isobutyronitrile, valeronitrile or capronitrile, more preferably acetonitrile.

The reagent for introduction of amidine groups is more preferably selected from the group consisting of trimethyl orthoformate, triethyl orthoformate, trimethyl orthoacetate, triethyl orthoacetate, methyl acetoacetate, ethyl acetoacetate, isopropyl acetoacetate, tert-butyl acetoacetate and acetonitrile.

With these reagents, cyclic amidines of the formula HZ are obtained in a particularly simple manner, which enable amidines of the formula (I) having particularly high catalytic activity.

The reaction is preferably conducted at elevated temperature, optionally under elevated pressure and optionally in the presence of a catalyst, wherein elimination products released from the reagent, such as alcohols, esters or amines, are preferably removed during or after the reaction, especially by means of distillation, optionally under reduced pressure.

Preferably, the ratio between the diamine and the reagent is chosen such that the reagent is fully converted in the reaction. More preferably, the diamine and the reagent are used in a molar ratio of about 1:1 to 1.5:1, especially 1:1 to 1.2:1.

If an ortho ester is used, the reaction is preferably effected at a temperature of 40 to 160° C., especially 60 to 140° C., the alcohol released preferably being removed by distillation. A catalyst is optionally used here, especially an acid.

If a 1,3-keto ester is used, the reaction is preferably effected at a temperature of 20 to 100° C., especially 40 to 80° C., the ester released preferably being removed by distillation. A catalyst is preferably used here, especially an acid, preferably a sulfonic acid.

If a nitrile is used, the reaction is preferably effected at a temperature of 60 to 180° C., especially 80 to 160° C., optionally under elevated pressure, the ammonia released preferably being removed by distillation. A catalyst is preferably used here, especially a Lewis acid, preferably boron trifluoride etherate, lithium perchlorate, zinc chloride, zinc (III) trifluoromethanesulfonate or lanthanum(III) trifluoromethanesulfonate.

In a preferred amidine of the formula (I), p is an integer from 1 to 4, preferably 1 or 2 or 3, especially 1 or 2, r is 0, Q' is

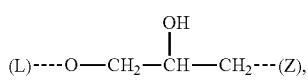

L is a p-valent hydrocarbyl radical which has an average molecular weight in the range from 15 to 1,500 g/mol and optionally contains ether oxygens and optionally an alkoxysilane group, and Z is a cyclic amidine group. Such an amidine especially has the formula (Ia).

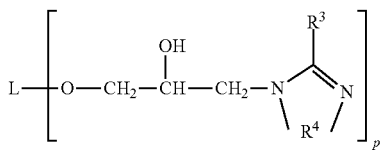

In this formula, L is preferably a radical selected from the group consisting of 2-ethylhexyl glycidyl ether, $C_8$- to $C_{10}$-alkyl glycidyl ether, $C_{12}$- to $C_{14}$-alkyl glycidyl ether, cresyl glycidyl ether, tert-butylphenyl glycidyl ether, cardanol glycidyl ether, butane-1,4-diol diglycidyl ether, hexane-1,6-diol diglycidyl ether, neopentyl glycol diglycidyl ether, polypropylene glycol diglycidyl ether having an average molecular weight in the range from 280 to 1,500 g/mol, bisphenol A diglycidyl ether, bisphenol F diglycidyl ether, 3-glycidoxypropyltrimethoxysilane and 3-glycidoxypropyltriethoxysilane, in each case after removal of the glycidoxy groups.

More preferably, p is 1 and L is triethoxysilylpropyl or trimethoxysilylpropyl.

Such an amidine is particularly suitable as catalyst for compositions containing silane groups, where it can be covalently bonded via the silane groups in the course of curing.

In a further preferred amidine of the formula (I), p is an integer from 1 to 4, r is 0, Q'is

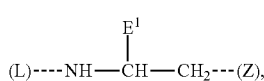

L is a p-valent hydrocarbyl radical which has an average molecular weight in the range from 15 to 5,000 g/mol, especially 15 to 2,000 g/mol, more preferably 87 to 500 g/mol, and especially has oxygen in the form of ester groups, and Z is a cyclic amidine group. Such an amidine especially has the formula (Ib).

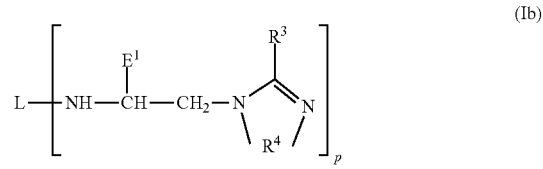

In a further preferred amidine of the formula (I), p is an integer from 1 to 3, r is 0, Q' is

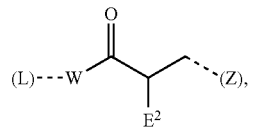

L is a p-valent hydrocarbyl radical which has an average molecular weight in the range from 15 to 5,000 g/mol, especially 15 to 2,000 g/mol, and optionally has oxygen or nitrogen or silicon in the form of ether, tertiary amino, ester, urethane, isocyanurate, biuret, allophanate and/or alkoxysilane groups, and Z is a cyclic amidine group, where, in the case that p=1, L and $R^5$ together may also be an optionally substituted alkylene radical which has 2 to 6 carbon atoms and optionally contains an ether oxygen. Such an amidine especially has the formula (Ic).

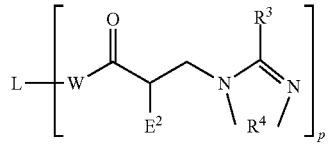

Preferably, $E^2$ here is a hydrogen radical or methyl radical.

Preferably, L here is either a radical selected from butyl, 2-ethylhexyl, trimethoxysilylpropyl, triethoxysilylpropyl, 1,2-ethylene, 3,6,9-trioxa-1,11-undecylene, 2,5-dimethyl-3,6-dioxa-1,8-nonylene, a polyoxyethylene radical having a molecular weight in the range from 200 to 2,000 g/mol, a polyoxypropylene radical having a molecular weight in the range from 200 to 2,000 g/mol, 1,4-butylene, 1,6-hexylene, 2,2-dimethyl-1,3-propylene, trimethylolpropane after removal of three hydroxyl groups, and polyurethane polymers having (meth)acrylate groups and having an average molecular weight in the range from 500 to 5,000 g/mol, especially from the reaction of 2-hydroxyethyl acrylate with polyurethane polymers containing isocyanate groups, or L and $R^5$ together are 3-oxa-1,5-pentylene.

In a further preferred amidine of the formula (I), p is 1, r is 0, Q' is

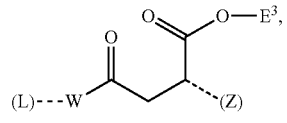

L is a monovalent hydrocarbyl radical having 1 to 8 carbon atoms and Z is a cyclic amidine group. Such an amidine especially has the formula (Id).

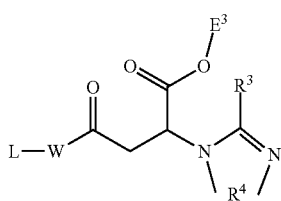
(Id)

Preferably, L and $E^3$ here are each the same radical.

The invention further provides for the use of an amidine of the formula (I) as described above as catalyst for the crosslinking of a curable composition. In this case, it accelerates the crosslinking or curing of the composition.

A suitable curable composition is especially
an epoxy resin composition, especially a high-temperature-curing system that crosslinks via dicyandiamide or carboxylic acids or carboxylic anhydrides, as used, for example, in adhesives, coatings or casting resins; or
a polyurethane composition, especially a two-component system that crosslinks by reaction of polyols with isocyanates, as used, for example, for adhesives, coverings, potting compounds, sealing joints, moldings or slabstock foams, or a one-component system having blocked isocyanate groups or blocked amino groups, as used, for example, in powder coatings, coil coatings, electrocoat materials or liquid paints; or
an epoxy resin/polyurethane composition; or
a cyanate ester resin composition; or
a composition containing silane groups.

Preferably, the curable composition is a polyurethane composition or a composition containing silane groups. In such a composition, the amidine of the formula (I) enables good storage stability and rapid curing.

A particularly advantageous use is for crosslinking of a composition containing silane groups, especially of a composition based on polymers containing silane groups. Compositions based on polymers containing silane groups cure rapidly even when the catalyst concentration is relatively low and do not have a tendency to migration-related defects such as separation, exudation or substrate soiling.

Particular preference is given to the use of the amidine of the formula (I) as catalyst for the crosslinking of a composition based on polymers containing silane groups that are selected from the group consisting of polyorganosiloxanes having terminal silane groups and organic polymers containing silane groups.

A polyorganosiloxane having terminal silane groups has the advantage that, in the cured state, it is particularly water- and light-stable and enables particularly flexible properties.

An organic polymer containing silane groups has the advantage of having particularly good adhesion properties on a multitude of substrates and being particularly inexpensive.

The invention thus further provides a curable composition comprising at least one amidine of the formula (I).

Preferably, the curable composition is an adhesive or a sealant or a coating.

Preferably, the curable composition further comprises at least one polymer containing silane groups.

A composition of this kind typically has good storability with no propensity to separation, and because of the low toxicity and low volatility of the amidine of the formula (I) allows a low hazard classification and enables low-emissions and low-odor products that cure rapidly and at the same time form a mechanically high-quality and durable material. A particularly advantageous circumstance here is that this material shows barely any propensity to migration-related defects such as exudation or substrate soiling, by contrast with compositions comprising catalysts according to the prior art, for example DBU or TMG. Compositions comprising such catalysts known from the prior art have a propensity to migration effects, which can be manifested prior to curing by separation and after curing by tacky and/or greasy surfaces and/or substrate soiling. Particularly the latter effects are extremely undesirable, since tacky and greasy surfaces are rapidly soiled and are difficult to paint over, and substrate contaminants can lead to lasting discoloration.

In a preferred embodiment, the polymer containing silane groups is a polyorganosiloxane having terminal silane groups.

A preferred polyorganosiloxane having terminal silane groups has the formula (IV)

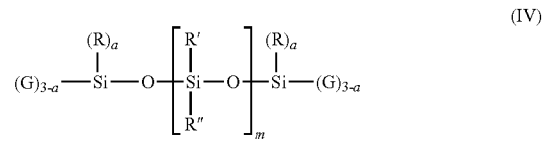
(IV)

where
R, R' and R" are each independently a monovalent hydrocarbyl radical having 1 to 12 carbon atoms;
G is a hydroxyl radical or an alkoxy, acetoxy, ketoximato, amido or enoxy radical having 1 to 13 carbon atoms;
a is 0, 1 or 2; and
m is an integer in the range from 50 to about 2,500.
R is preferably methyl, vinyl or phenyl.
R' and R" are preferably each independently an alkyl radical having 1 to 5, preferably 1 to 3, carbon atoms, especially methyl.
G is preferably a hydroxyl radical or an alkoxy or ketoximato radical having 1 to 6 carbon atoms, especially a hydroxyl, methoxy, ethoxy, methylethylketoximato or methylisobutylketoximato radical.
More preferably, G is a hydroxyl radical.
a is preferably 0 or 1, especially 0.
In addition, m is preferably chosen such that the polyorganosiloxane of the formula (IV) has a viscosity at room temperature in the range from 100 to 500,000 mPa·s, especially from 1000 to 100,000 mPa·s.

Polyorganosiloxanes of the formula (IV) are easy to handle and crosslink with moisture and/or silane crosslinkers to give solid silicone polymers having elastic properties.

Suitable commercially available polyorganosiloxanes of the formula (IV) are available, for example, from Wacker, Momentive Performance Material, GE Advanced Materials, Dow Corning, Bayer or Shin Etsu.

Preferably, the composition comprises, in addition to the polyorganosiloxane having terminal silane groups, a silane crosslinker, especially a silane of the formula (V),

(V)

where
R''' is a monovalent hydrocarbyl radical having 1 to 12 carbon atoms,

G' is a hydroxyl radical or is an alkoxy, acetoxy, ketoximato, amido or enoxy radical having 1 to 13 carbon atoms; and q has a value of 0, 1 or 2, especially 0 or 1.

Particularly suitable silanes of the formula (V) are methyltrimethoxysilane, ethyltrimethoxysilane, propyltrimethoxysilane, vinyltrimethoxysilane, methyltriethoxysilane, vinyltriethoxysilane, phenyltriethoxysilane, tetramethoxysilane, tetraethoxysilane, methyltris(methylethylketoximo)silane, vinyltris(methylethylketoximo)silane and methyltris(isobutylketoximo)silane.

In a further preferred embodiment, the polymer containing silane groups is an organic polymer containing silane groups, especially a polyolefin, polyester, polyamide, poly(meth)acrylate or polyether or a mixed form of these polymers, each of which bears one or preferably more than one silane group. The silane groups may be in pendant positions in the chain or in terminal positions and are bonded to the organic polymer via a carbon atom.

More preferably, the organic polymer containing silane groups is a polyolefin containing silane groups or a polyester containing silane groups or a poly(meth)acrylate containing silane groups or a polyether containing silane groups or a mixed form of these polymers.

Most preferably, the organic polymer containing silane groups is a polyether containing silane groups.

The silane groups present in the organic polymer containing silane groups are preferably alkoxysilane groups, especially alkoxysilane groups of the formula (VI)

where
$R^{14}$ is a linear or branched, monovalent hydrocarbyl radical having 1 to 5 carbon atoms, especially methyl or ethyl or isopropyl;
$R^{15}$ is a linear or branched, monovalent hydrocarbyl radical having 1 to 8 carbon atoms, especially methyl or ethyl; and
x is a value of 0 or 1 or 2, preferably 0 or 1, especially 0. More preferably $R^{14}$ is methyl or ethyl.

Particular preference is given to trimethoxysilane groups, dimethoxymethylsilane groups or triethoxysilane groups.

In this context, methoxysilane groups have the advantage that they are particularly reactive, and ethoxysilane groups have the advantage that they are toxicologically advantageous and particularly storage-stable.

The organic polymer containing silane groups has an average of preferably 1.3 to 4, especially 1.5 to 3, more preferably 1.7 to 2.8, silane groups per molecule.

The silane groups are preferably terminal.

The organic polymer containing silane groups preferably has an average molecular weight in the range from 1,000 to 30,000 g/mol, especially from 2,000 to 20,000 g/mol. The organic polymer containing silane groups preferably has a silane equivalent weight of 300 to 25,000 g/eq, especially of 500 to 15,000 g/eq.

The organic polymer containing silane groups may be solid or liquid at room temperature. It is preferably liquid at room temperature.

Most preferably, the organic polymer containing silane groups is a polyether containing silane groups which is liquid at room temperature, where the silane groups are especially dialkoxysilane groups and/or trialkoxysilane groups, more preferably trimethoxysilane groups or triethoxysilane groups.

Processes for preparing polyethers containing silane groups are known to the person skilled in the art.

In a preferred process, polyethers containing silane groups are obtainable from the reaction of polyethers containing allyl groups with hydrosilanes, optionally with chain extension using, for example, diisocyanates.

In a further preferred process, polyethers containing silane groups are obtainable from the copolymerization of alkylene oxides and epoxysilanes, optionally with chain extension using, for example, diisocyanates.

In a further preferred process, polyethers containing silane groups are obtainable from the reaction of polyether polyols with isocyanatosilanes, optionally with chain extension using diisocyanates.

In a further preferred process, polyethers containing silane groups are obtainable from the reaction of polyethers containing isocyanate groups, especially NCO-terminated urethane polyethers from the reaction of polyether polyols with a superstoichiometric amount of polyisocyanates, with aminosilanes, hydroxysilanes or mercaptosilanes. Polyethers containing silane groups from this process are particularly preferred. This process enables the use of a multitude of inexpensive starting materials of good commercial availability, by means of which it is possible to obtain different polymer properties, for example high extensibility, high strength, low modulus of elasticity, low glass transition point or high weathering resistance.

More preferably, the polyether containing silane groups is obtainable from the reaction of NCO-terminated urethane polyethers with aminosilanes or hydroxysilanes. Suitable NCO-terminated urethane polyethers are obtainable from the reaction of polyether polyols, especially polyoxyalkylenediols or polyoxyalkylenetriols, preferably polyoxypropylenediols or polyoxypropylenetriols, with a superstoichiometric amount of polyisocyanates, especially diisocyanates.

Preferably, the reaction between the polyisocyanate and the polyether polyol is conducted with exclusion of moisture at a temperature of 50° C. to 160° C., optionally in the presence of suitable catalysts, with metered addition of the polyisocyanate in such a way that the isocyanate groups thereof are present in a stoichiometric excess in relation to the hydroxyl groups of the polyol. More particularly, the excess of polyisocyanate is chosen such that a content of free isocyanate groups of 0.1% to 5% by weight, preferably 0.2% to 4% by weight, more preferably 0.3% to 3% by weight, based on the overall polymer, remains in the resulting urethane polyether after the reaction of all hydroxyl groups. Preferred diisocyanates are selected from the group consisting of hexamethylene 1,6-diisocyanate (HDI), 1-isocyanato-3,3,5-trimethyl-5-isocyanatomethylcyclohexane (isophorone diisocyanate or IPDI), tolylene 2,4- and 2,6-diisocyanate and any desired mixtures of these isomers (TDI) and diphenylmethane 4,4'-, 2,4'- and 2,2'-diisocyanate and any desired mixtures of these isomers (MDI). Particular preference is given to IPDI or TDI. Most preferred is IPDI. In this way, polyethers containing silane groups with particularly good lightfastness are obtained.

Especially suitable as polyether polyols are polyoxyalkylenediols or polyoxyalkylenetriols having a degree of unsaturation lower than 0.02 meq/g, especially lower than 0.01 meq/g, and an average molecular weight in the range from 400 to 25,000 g/mol, especially 1000 to 20,000 g/mol.

As well as polyether polyols, it is also possible to use portions of other polyols, especially polyacrylate polyols, and low molecular weight diols or triols.

Suitable aminosilanes for the reaction with an NCO-terminated urethane polyether are primary and secondary aminosilanes. Preference is given to 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts formed from primary aminosilanes such as 3-aminopropyltrimethoxysilane, 3-aminopropyldimethoxymethylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinate. Likewise suitable are analogs of the aminosilanes mentioned with ethoxy or isopropoxy groups in place of the methoxy groups on the silicon.

Suitable hydroxysilanes for the reaction with an NCO-terminated urethane polyether are especially obtainable from the addition of aminosilanes onto lactones or onto cyclic carbonates or onto lactides.

Aminosilanes suitable for this purpose are especially 3-aminopropyltrimethoxysilane, 3-aminopropyltriethoxysilane, 4-aminobutyltrimethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane or 2-aminoethyltriethoxysilane. Particular preference is given to 3-aminopropyltrimethoxysilane, 3-aminopropyltriethoxysilane, 4-amino-3,3-dimethylbutyltrimethoxysilane or 4-amino-3,3-dimethylbutyltriethoxysilane.

Suitable lactones are especially γ-valerolactone, γ-octalactone, δ-decalactone, and ε-decalactone, especially γ-valerolactone.

Suitable cyclic carbonates are especially 4,5-dimethyl-1,3-dioxolan-2-one, 4,4-dimethyl-1,3-dioxolan-2-one, 4-ethyl-1,3-dioxolan-2-one, 4-methyl-1,3-dioxolan-2-one or 4-(phenoxymethyl)-1,3-dioxolan-2-one.

Suitable lactides are especially 1,4-dioxane-2,5-dione (lactide formed from 2-hydroxyacetic acid, also called "glycolide"), 3,6-dimethyl-1,4-dioxane-2,5-dione (lactide formed from lactic acid, also called "lactide") and 3,6-diphenyl-1,4-dioxane-2,5-dione (lactide formed from mandelic acid).

Preferred hydroxysilanes which are obtained in this way are N-(3-triethoxysilylpropyl)-2-hydroxypropanamide, N-(3-trimethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxydecanamide and N-(3-triethoxysilylpropyl)-2-hydroxypropyl carbamate.

In addition, suitable hydroxysilanes are also obtainable from the addition of aminosilanes onto epoxides or from the addition of amines onto epoxysilanes.

Preferred hydroxysilanes which are obtained in this way are 2-morpholino-4(5)-(2-trimethoxysilylethyl)cyclohexan-1-ol, 2-morpholino-4(5)-(2-triethoxysilyl-ethyl)cyclohexan-1-ol or 1-morpholino-3-(3-(triethoxysilyl)propoxy)propan-2-ol.

Further suitable polyethers containing silane groups are commercially available products, especially the following: MS Polymer™ (from Kaneka Corp.; especially the S203H, S303H, S227, S810, MA903 and S943 products); MS Polymer™ or Silyl™ (from Kaneka Corp.; especially the SAT010, SAT030, SAT200, SAX350, SAX400, SAX725, MAX450, MAX951 products); Excestar® (from Asahi Glass Co. Ltd.; especially the S2410, S2420, S3430, S3630 products); SPUR+* (from Momentive Performance Materials; especially the 1010LM, 1015LM, 1050MM products); Vorasil™ (from Dow Chemical Co.; especially the 602 and 604 products); Desmoseal® (from Bayer MaterialScience AG; especially the S XP 2458, S XP 2636, S XP 2749, S XP 2774 and S XP 2821 products), TEGOPAC® (from Evonik Industries AG; especially the Seal 100, Bond 150, Bond 250 products), Polymer ST (from Hanse Chemie AG/Evonik Industries AG, especially the 47, 48, 61, 61 LV, 77, 80, 81 products); Geniosil® STP (from Wacker Chemie AG; especially the E10, E15, E30, E35 products).

Particularly preferred organic polymers containing silane groups have end groups of the formula (VII)

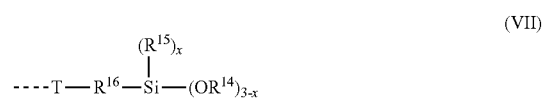

(VII)

where $R^{16}$ is a linear or branched divalent hydrocarbyl radical which has 1 to 12 carbon atoms and optionally has cyclic and/or aromatic moieties and optionally one or more heteroatoms, especially one or more nitrogen atoms;

T is a divalent radical selected from —O—, —S—, —N($R^{17}$)—, —O—CO—N($R^{17}$)—, —N($R^{17}$)—CO—O— and —N($R^{17}$)—CO—N($R^{17}$)—, where $R^{17}$ is a hydrogen radical or a linear or branched hydrocarbyl radical which has 1 to 20 carbon atoms and optionally has cyclic moieties, and which optionally has an alkoxysilane, ether or carboxylic ester group; and $R^{14}$, $R^{15}$ and x have the definitions already given.

Preferably, $R^{16}$ is 1,3-propylene or 1,4-butylene, where butylene may be substituted by one or two methyl groups.

More preferably, $R^{16}$ is 1,3-propylene.

Preferably, the amidine of the formula (I) is present in the curable composition in such an amount that the concentration of amidine groups based on the amount of the crosslinkable polymer is in the range from 0.1 to 50 mmol/100 g of polymer, preferably 0.2 to 50 mmol/100 g of polymer, especially 0.5 to 20 mmol/100 g.

Such a composition has good storability and rapid curing.

In addition to the amidine of the formula (I), the composition may comprise further catalysts, especially for the crosslinking of silane groups. Suitable further catalysts are especially metal compounds and/or basic nitrogen or phosphorus compounds.

Suitable metal compounds are especially compounds of tin, titanium, zirconium, aluminum or zinc, especially diorganotin(IV) compounds such as, in particular, dibutyltin(IV) diacetate, dibutyltin(IV) dilaurate, dibutyltin(IV) dineodecanoate or dibutyltin(IV) bis(acetylacetonate) and dioctyltin(IV) dilaurate, and also titanium(IV) or zirconium(IV) or aluminum(III) or zinc(II) complexes, especially with alkoxy, carboxylate, 1,3-diketonate, 1,3-ketoesterate or 1,3-ketoamidate ligands.

Suitable basic nitrogen or phosphorus compounds are especially imidazoles, pyridines, phosphazene bases or preferably amines, hexahydrotriazines, biguanides, guanidines or further amidines.

Suitable amines are, in particular, alkyl-, cycloalkyl- or aralkylamines such as triethylamine, triisopropylamine, 1-butylamine, 2-butylamine, tert-butylamine, 3-methyl-1-butylamine, 3-methyl-2-butylamine, dibutylamine, tributylamine, hexylamine, dihexylamine, cyclohexylamine, dicyclohexylamine, dimethylcyclohexylamine, benzylamine, dibenzylamine, dimethylbenzylamine, octylamine, 2-ethylhexylamine, di-(2-ethylhexyl)amine, laurylamine, N,N-dimethyllaurylamine, stearylamine, N,N-dimethylstearylamine; fatty amines derived from natural fatty acid mixtures, such as, in particular, cocoalkylamine, N, N-dimethylcocoalkylamine, $C_{16-22}$-alkylamine, N, N-dimethyl-$C_{16-22}$-alkylamine, soyaalkylamine, N,N-dimethylsoyaalkylamine, oleylamine, N,N-dimethyloleylamine, tallowalkylamine or N,N-dimethyltallowalkylamine, obtainable for example under the trade names Armeen® (from Akzo Nobel) or Rofamin® (from Ecogreen Oleochemicals); aliphatic, cycloaliphatic or araliphatic diamines such as ethylenediamine, butanediamine, hexamethylenediamine, dodecanediamine, neopentanediamine, 2-methylpentamethylenediamine (MPMD), 2,2(4),4-trimethylhexamethylenediamine (TMD), isophoronediamine (IPD), 2,5(2,6)-bis(aminomethyl)bicyclo[2.2.1]heptane (NBDA), xylylene-1,3-diamine (MXDA), N,N'-di(tert-butyl)ethylenediamine, N,N,N',N'-tetramethylethylenediamine, N,N,N',N'-tetramethylpropylenediamine, N,N,N',N'-tetramethylhexamethylenediamine, 3-dimethylaminopropylamine, 3-(methylamino)propylamine, 3-(cyclohexylamino)propylamine, piperazine, N-methylpiperazine, N,N'-dimethylpiperazine, 1,4-diazabicyclo[2.2.2]octane, fatty polyamines such as N-cocoalkylpropane-1,3-diamine, N-oleylpropane-1,3-diamine, N-soyaalkylpropane-1,3-diamine, N-tallowalkylpropane-1,3-diamine or N—($C_{16-22}$-alkyl)propane-1,3-diamine, obtainable for example under the trade name Duomeen® (from Akzo Nobel); polyalkyleneamines such as diethylenetriamine, dipropylenetriamine, triethylenetetramine (TETA), tetraethylenepentamine (TEPA), pentamethylenehexamine (PEHA), 3-(2-aminoethyl)aminopropylamine, N,N'-bis(3-aminopropyl)ethylenediamine, N-(3-aminopropyl)-N-methylpropanediamine, bis(3-dimethylaminopropyl)amine, N-(3-dimethylaminopropyl) propylene-1,3-diamine, N-(2-aminoethyl)piperazine (N-AEP), N-(2-aminopropyl)piperazine, N,N'-di-(2-aminoethyl)piperazine, 1-methyl-4-(2-dimethylaminoethyl)piperazine, N,N,N',N'',N''-pentamethyldiethylenetriamine, N,N,N',N'',N''-pentamethyldipropylenetriamine, polyethyleneimines obtainable for example under the trade names Lupasol® (from BASF) and Epomin® (from Nippon Shokubai); ether amines, such as, in particular, 2-methoxyethylamine, 2-ethoxyethylamine, 3-methoxypropylamine, 3-ethoxypropylamine, 3-(2-ethylhexyloxy)propylamine, 3-(2-methoxyethoxy)propylamine, 2(4)-methoxyphenylethylamine, morpholine, N-methylmorpholine, N-ethylmorpholine, 2-aminoethylmorpholine, bis(2-aminoethyl) ether, bis(dimethylaminoethyl) ether, bis(dimorpholinoethyl) ether, N, N, N'-trimethyl-N'-hydroxyethylbis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, or 2-aminopropyl-terminated glycols, of the kind obtainable for example under the trade name Jeffamine® (from Huntsman); amino alcohols, such as, in particular, ethanolamine, isopropanolamine, diethanolamine, diisopropanolamine, triethanolamine, triisopropanolamine, N-butylethanolamine, diglycolamine, N,N-diethylethanolamine, N-methyldiethanolamine, N-methyldiisopropylamine, N,N,N'-trimethylaminoethylethanolamine, N-(3-dimethylaminopropyl)-N,N-diisopropanolamine, N,N-bis(3-dimethylaminopropyl)-N-isopropanolamine, 2-(2-dimethylaminoethoxy)ethanolamine, or adducts of mono- and polyamines with epoxides or diepoxides; amines containing phenol groups, such as, in particular, condensation products of phenols, aldehydes, and amines (so-called Mannich bases and phenalkamines) such as, in particular, 2-(dimethylaminomethyl)phenol, 2,4,6-tris(dimethylaminomethyl)phenol, or polymers of phenol, formaldehyde, and N,N-dimethylpropane-1,3-diamine, and also phenalkamines obtainable commercially under the brand names Cardolite® (from Cardolite), Aradur® (from Huntsman), and Beckopox® (from Cytec); polyamines containing amide groups, so-called polyamidoamines, of the kind available commercially, for example, under the brand names Versamid® (from Cognis), Aradur® (from Huntsman), Euretek® (from Huntsman) or Beckopox® (from Cytec); or aminosilanes, such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyl-methyldimethoxysilane, N-(2-aminoethyl)-N'-[3-(trimethoxysilyl)propyl]ethylenediamine or their analogs with ethoxy rather than the methoxy groups on the silicon.

Suitable hexahydrotriazines are especially 1,3,5-hexahydrotriazine or 1,3,5-tris(3-(dimethylamino)propyl)hexahydrotriazine.

Suitable biguanides are especially biguanide, 1-butylbiguanide, 1,1-dimethylbiguanide, 1-butylbiguanide, 1-phenylbiguanide or 1-(o-tolyl)biguanide (OTBG).

Suitable guanidines are especially 1-butylguanidine, 1,1-dimethylguanidine, 1,3-dimethylguanidine, 1,1,3,3-tetramethylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethylguanidine, 1,5,7-triazabicyclo[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine or 2-guanidinobenzimidazole.

Suitable further amidines are especially 1,8-diazabicyclo[5.4.0]undec-7-ene (DBU), 1,5-diazabicyclo[4.3.0]non-5-ene (DBN), 6-dibutylamino-1,8-diazabicyclo[5.4.0]undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1,2-dimethyl-1,4,5,6-tetrahydropyrimidine, 2,5,5-trimethyl-1,4,5,6-tetrahydropyrimidine, N-(3-trimethoxysilylpropyl)-4,5-dihydroimidazole or N-(3-triethoxy-silylpropyl)-4,5-dihydroimidazole.

In addition, the composition may comprise, as cocatalyst, an acid, especially a carboxylic acid. Preference is given to aliphatic carboxylic acids such as formic acid, lauric acid, stearic acid, isostearic acid, oleic acid, 2-ethyl-2,5-dimethylcaproic acid, 2-ethylhexanoic acid, neodecanoic acid, fatty acid mixtures from the hydrolysis of natural fats and oils or di- and polycarboxylic acids, especially poly(meth)acrylic acids.

In a preferred embodiment, the composition is essentially free of organotin compounds. Organotin-free compositions are advantageous in terms of protection of health and protection of the environment. More particularly, the tin content of the curable composition is less than 0.1% by weight, especially less than 0.05% by weight.

In a further preferred embodiment, the composition comprises a combination of at least one amidine of the formula (I) and at least one organotin compound, especially a diorganotin(IV) compound such as those mentioned above. Such a composition has a high curing rate even in the case of a low tin content, which is advantageous for toxicological and environmental reasons.

In one embodiment, the composition additionally comprises, as well as the amidine of the formula (I), at least one organotitanate. A combination of an amidine of the formula (I) and an organotitanate has particularly high catalytic activity. This enables rapid curing with a comparatively small use amount of organotitanate.

Suitable organotitanates are especially titanium(IV) complexes.

Preferred organotitanates are especially selected from
titanium(IV) complexes having two 1,3-diketonate ligands, especially 2,4-pentanedionate (=acetylacetonate), and two alkoxide ligands;
titanium(IV) complexes having two 1,3-ketoesterate ligands, especially ethylacetoacetate, and two alkoxide ligands;
titanium(IV) complexes having one or more aminoalkoxide ligands, especially triethanolamine or 2-((2-aminoethyl)amino)ethanol, and one or more alkoxide ligands;
titanium(IV) complexes having four alkoxide ligands;
and more highly condensed organotitanates, especially oligomeric titanium(IV) tetrabutoxide, also referred to as polybutyl titanate;
where suitable alkoxide ligands are especially isobutoxy, n-butoxy, isopropoxy, ethoxy and 2-ethylhexoxy.

Especially suitable are the commercially available products Tyzor® AA, GBA, GBO, AA-75, AA-65, AA-105, DC, BEAT, BTP, TE, TnBT, K™, TOT, TPT or IBAY (all from Dorf Ketal); Tytan PBT, TET, X85, TAA, ET, S2, S4 or S6 (all from Borica Company Ltd.) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Very particularly suitable organotitanates are selected from bis(ethylaceto-acetato)diisobutoxytitanium(IV) (commercially available, for example, as Tyzor® IBAY from Dorf Ketal), bis(ethylacetoacetato)diisopropoxytitanium (IV) (commercially available, for example, as Tyzor® DC from Dorf Ketal), bis(acetylacetonato)diisopropoxytitanium (IV), bis(acetylacetonato)diisobutoxy-titanium(IV), tris (oxyethyl)amine-isopropoxy-titanium(IV), bis[tris(oxyethyl)-amine]diisopropoxytitanium(IV), bis(2-ethylhexane-1,3-dioxy)titanium(IV), tris[2-((2-aminoethyl)amino) ethoxy]ethoxytitanium(IV), bis(neopentyl(diallyl)oxy)-diethoxytitanium(IV), titanium(IV) tetrabutoxide, tetra(2-ethylhexyloxy) titanate, tetra(isopropoxy) titanate and polybutyl titanate.

Most preferred are bis(ethylacetoacetato)diisobutoxytitanium(IV) or bis(ethylacetoacetato)diisopropoxytitanium (IV).

The composition may comprise further constituents, especially the following auxiliaries and additives:

adhesion promoters and/or crosslinkers, especially aminosilanes such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)-propyl] ethylenediamine or the analogs thereof with ethoxy in place of methoxy groups, and also N-phenyl-, N-cyclohexyl- or N-alkylaminosilanes, mercaptosilanes, epoxysilanes, (meth)acryloylsilanes, anhydridosilanes, carbamatosilanes, alkylsilanes or iminosilanes, oligomeric forms of these silanes, adducts formed from primary aminosilanes with epoxysilanes or (meth)acryloylsilanes or anhydridosilanes, amino-functional alkylsilsesquioxanes, especially amino-functional methylsilsesquioxane or amino-functional propylsilsesquioxane. Especially suitable are 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, 3-glycidoxypropyltrimethoxysilane, 3-glycidoxypropyltriethoxysilane or 3-ureidopropyltrimethoxysilane, or oligomeric forms of these silanes;
desiccants, especially tetraethoxysilane, vinyltrimethoxysilane, vinyltriethoxysilane or organoalkoxysilanes having a functional group in the α position to the silane group, especially N-(methyldimethoxysilylmethyl)-O-methylcarbamate, (methacryloyloxymethyl)silanes, methoxymethylsilanes, orthoformic esters, calcium oxide or molecular sieves, especially vinyltrimethoxysilane or vinyltriethoxysilane;
plasticizers, especially trialkylsilyl-terminated polydialkylsiloxanes, preferably trimethylsilyl-terminated polydimethylsiloxanes, especially having viscosities in the range from 10 to 1,000 mPa·s, or corresponding compounds in which some of the methyl groups have been replaced by other organic groups, especially phenyl, vinyl or trifluoropropyl groups, called reactive plasticizers, in the form of monofunctional polysiloxanes, i.e. those that are reactive at one end, carboxylic esters such as phthalates, especially dioctyl phthalate, bis(2-ethylhexyl) phthalate, bis(3-propylheptyl) phthalate, diisononyl phthalate or diisodecyl phthalate, diesters of ortho-cyclohexane-dicarboxylic acid, especially diisononyl 1,2-cyclohexanedicarboxylate, adipates, especially dioctyl adipate, bis(2-ethylhexyl) adipate, azelates, especially bis(2-ethylhexyl) azelate, sebacates, especially bis(2-ethylhexyl) sebacate or diisononyl sebacate, polyols, especially polyoxyalkylene polyols or polyester polyols, glycol ethers, glycol esters, organic phosphoric or sulfonic esters, sulfonamides, polybutenes, or fatty acid methyl or ethyl esters derived from natural fats or oils, also called "biodiesel", plasticizers containing siloxane groups being particularly suitable for polymers containing silane groups in the form of polyorganosiloxanes;
solvents;
inorganic or organic fillers, especially natural, ground or precipitated calcium carbonates, optionally coated with fatty acids, especially stearic acid, baryte (heavy spar), talcs, quartz flours, quartz sand, dolomites, wollastonites, kaolins, calcined kaolins, mica (potassium aluminum silicate), molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow spheres;
fibers, especially glass fibers, carbon fibers, metal fibers, ceramic fibers or polymer fibers such as polyamide fibers or polyethylene fibers;
dyes;
pigments, especially titanium dioxide or iron oxides;
rheology modifiers, especially thickeners, especially sheet silicates such as bentonites, derivatives of castor oil, hydrogenated castor oil, polyamides, polyurethanes, urea compounds, fumed silicas, cellulose ethers or hydrophobically modified polyoxyethylenes;

stabilizers against oxidation, heat, light or UV radiation;
natural resins, fats or oils such as rosin, shellac, linseed oil, castor oil or soya oil;
non-reactive polymers such as, in particular, homo- or copolymers of unsaturated monomers, especially from the group comprising ethylene, propylene, butylene, isobutylene, isoprene, vinyl acetate or alkyl (meth) acrylates, especially polyethylenes (PE), polypropylenes (PP), polyisobutylenes, ethylene-vinyl acetate copolymers (EVA) or atactic poly-α-olefins (APAO);
flame-retardant substances, especially the already mentioned fillers aluminum hydroxide and magnesium hydroxide, or, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis (diphenyl phosphate) or ammonium polyphosphates;
surface-active substances, especially wetting agents, leveling agents, deaerating agents or defoamers;
biocides, especially algicides, fungicides or substances that inhibit fungal growth;
and other substances customarily used in curable compositions. It may be advisable to chemically or physically dry certain constituents before mixing them into the composition.

In a preferred embodiment, the composition comprises at least one desiccant and at least one adhesion promoter and/or crosslinker.

In a preferred embodiment, the composition does not comprise any phthalates as plasticizers. Such compositions are toxicologically advantageous and have fewer problems with migration effects.

The composition is preferably produced and stored with exclusion of moisture.

Typically, it is storage-stable with exclusion of moisture in a suitable package or arrangement, such as, more particularly, a bottle, a canister, a pouch, a bucket, a vat or a cartridge.

The composition may take the form of a one-component or of a multi-component, especially two-component, composition.

In the present document, "one-component" refers to a composition in which all constituents of the composition are stored in a mixture in the same container and which is curable with moisture.

In the present document, "two-component" refers to a composition in which the constituents of the composition are present in two different components which are stored in separate containers. Only shortly before or during the application of the composition are the two components mixed with one another, whereupon the mixed composition cures, optionally under the action of moisture.

If the composition comprises a polyorganosiloxane having terminal silane groups, preference is given either to a one-component composition, also referred to as RTV-1, or to a two-component composition, also referred to as RTV-2. In the case of an RTV-2 composition, the polyorganosiloxane having terminal silane groups is preferably a constituent of the first component, and a silane crosslinker, especially a silane crosslinker of the formula (VI), is preferably a constituent of the second component. The amidine of the formula (I) may be present in the first and/or the second component.

If the composition comprises an organic polymer containing silane groups, the composition is preferably a one-component composition.

Any second or optionally further components is/are mixed with the first component prior to or on application, especially by means of a static mixer or by means of a dynamic mixer.

The composition is especially applied at ambient temperature, preferably within a temperature range between 0° C. and 45° C., especially 5° C. to 35° C., and also cures under these conditions.

On application, the crosslinking reaction of the silane groups commences, if appropriate under the influence of moisture. Silane groups present can condense with silanol groups present to give siloxane groups (Si—O—Si groups).

Silane groups present can also be hydrolyzed on contact with moisture to give silanol groups (Si—OH groups) and form siloxane groups (Si—O—Si groups) through subsequent condensation reactions. As a result of these reactions, the composition ultimately cures. The amidine of the formula (I) accelerates this curing.

If water is required for the curing, this can either come from the air (air humidity), or else the composition can be contacted with a water-containing component, for example by painting, for example with a smoothing agent, or by spraying, or water or a water-containing component can be added to the composition on application, for example in the form of a water-containing or water-releasing liquid or paste. A paste is especially suitable if the composition itself is in the form of a paste.

In the case of curing by means of air humidity, the composition cures from the outside inward, at first forming a skin on the surface of the composition. What is called the skin time is a measure of the curing rate of the composition. The speed of curing is generally determined by various factors, for example the availability of water, temperature, etc.

The composition is suitable for a multitude of uses, especially as a paint, varnish or primer, as a resin for production of fiber composites, as a rigid foam, flexible foam, molding, elastomer, fiber, film or membrane, as a potting compound, sealant, adhesive, covering, coating or paint for construction and industrial applications, for example as a seam seal, cavity seal, electrical insulation compound, spackling compound, joint sealant, weld or crimp seam sealant, assembly adhesive, bodywork adhesive, glazing adhesive, sandwich element adhesive, laminating adhesive, laminate adhesive, packaging adhesive, wood adhesive, parquet adhesive, anchoring adhesive, floor covering, floor coating, balcony coating, roof coating, concrete protection coating, parking garage coating, seal, pipe coating, anticorrosion coating, textile coating, damping element, sealing element or spackling compound.

The composition is particularly suitable as an adhesive and/or sealant, especially for joint sealing and for elastic adhesive bonds in construction and industrial applications, and as elastic coating with crack-bridging properties, especially for protection and/or sealing of, for example, roofs, floors, balconies, parking decks or concrete pipes.

The composition is thus preferably an adhesive or a sealant or a coating.

A composition of this kind typically comprises plasticizers, fillers, adhesion promoters and/or crosslinkers and desiccants, and optionally further auxiliaries and additives.

For an application as adhesive or sealant, the composition preferably has a pasty consistency with structurally viscous properties. Such a pasty sealant or adhesive is especially applied to a substrate from standard cartridges which are operated manually, by means of compressed air or with a battery, or from a vat or hobbock by means of a delivery pump or an extruder, optionally by means of an application robot.

For an application as coating, the composition preferably has a liquid consistency at room temperature with self-leveling properties. It may be slightly thixotropic, such that the coating is applicable to sloping to vertical surfaces without flowing away immediately. It is especially applied by means of a roller or brush or by pouring-out and distribution by means, for example, of a roller, a scraper or a notched trowel.

On application, the composition is preferably applied to at least one substrate. Suitable substrates are especially
- glass, glass ceramic, concrete, mortar, brick, tile, gypsum and natural rocks such as limestone, granite or marble;
- metals or alloys such as aluminum, iron, steel and non-ferrous metals, and also surface-finished metals or alloys such as galvanized or chromed metals;
- leather, textiles, paper, wood, woodbase materials bonded with resins, for example phenolic, melamine or epoxy resins, resin-textile composites and further polymer composites;
- plastics such as polyvinyl chloride (rigid and flexible PVC), acrylonitrile-butadiene-styrene copolymers (ABS), polycarbonate (PC), polyamide (PA), polyesters, poly(methyl methacrylate) (PMMA), epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), and also fiber-reinforced plastics such as carbon fiber-reinforced plastics (CFP), glass fiber-reinforced plastics (GFP) and sheet molding compounds (SMC), where the plastics may preferably have been surface-treated by means of plasma, corona or flames;
- coated substrates such as powder-coated metals or alloys;
- paints or varnishes, especially automotive topcoats.

If required, the substrates can be pretreated prior to the application of the composition, especially by chemical and/or physical cleaning methods or by the application of an adhesion promoter, an adhesion promoter solution or a primer.

The composition is particularly suitable for contact with substrates that are particularly sensitive to defects caused by migrating substances, especially by the formation of discoloration or specks. These are, in particular, fine-pore substrates such as marble, limestone or other natural stones, gypsum, cement mortar or concrete, but also plastics. Especially on PVC, severe discoloration is observed in the presence of catalysts, for example DBU or TMG, and cannot be removed by cleaning. No such effects are observed with the amidine of the formula (I).

It is possible to bond or seal two identical or two different substrates, especially the aforementioned substrates.

After the curing of the composition with water, especially in the form of air humidity, and/or with at least one suitable crosslinker, a cured composition is obtained.

The use of the composition gives rise to an article which especially has been bonded, sealed or coated with the composition. The article is especially a built structure, especially a structure built by structural engineering or civil engineering, an industrially manufactured good or a consumable good, especially a window, a domestic appliance or a mode of transport such as, more particularly, an automobile, a bus, a truck, a rail vehicle, a ship, an aircraft or a helicopter; or the article may be an installable component thereof.

EXAMPLES

Adduced hereinafter are working examples which are intended to elucidate the invention described in detail. It will be appreciated that the invention is not restricted to these described working examples.

"Standard climatic conditions" refer to a temperature of 23±1° C. and a relative air humidity of 50±5%.

"EEW" stands for epoxy equivalent weight.

$^1$H NMR spectra were measured on a spectrometer of the Bruker Ascend 400 type at 400.14 MHz; the chemical shifts δ are reported in ppm relative to tetramethylsilane (TMS). Coupling constants J are reported in Hz. No distinction was made between true coupling and pseudo-coupling patterns.

Infrared spectra (FT-IR) were measured on a Nicolet iS5 FT-IR instrument from Thermo Scientific equipped with a horizontal ATR measurement unit with a diamond crystal. Liquid samples were applied undiluted as films; solid samples were dissolved in $CH_2Cl_2$. The absorption bands are reported in wavenumbers ($cm^{-1}$) (measurement window: 4000-650 $cm^{-1}$).

The skin time (ST) was determined by applying a few grams of the composition to cardboard in a layer thickness of about 2 mm and measuring, under standard climatic conditions, the time until, when the surface of the composition was gently tapped by means of an LDPE pipette, there were for the first time no residues remaining any longer on the pipette.

The characteristics of the surface were tested by touch.

The mechanical properties of tensile strength, elongation at break and modulus of elasticity (at 0-5% and at 0-50% or 0-100% elongation) were measured in accordance with DIN EN 53504 at a pulling speed of 200 mm/min.

Functional Compounds Used:
PGE phenyl glycidyl ether (from Sigma-Aldrich)
GLYEO 3-glycidoxypropyltriethoxysilane (Dynasylan® GLYEO, from Evonik)
TBA tert-butyl acrylate (from Sigma-Aldrich)
THFMA tetrahydrofurfuryl methacrylate (from Sigma-Aldrich)
TMPTA 1,1,1-trimethylolpropane triacrylate (SR-351, from Sartomer)
Y-9936 3-methacryloyloxypropyltriethoxysilane (Silquest® Y-9936, from Momentive)
NAM 4-acryloylmorpholine (from Sigma-Aldrich)
DEM diethyl maleate (from Sigma-Aldrich)

Preparation of Amidines of the Formula HZ

Amidine HZ-1: 2-Methyl-1
1,4,5,6-tetrahydropyrimidine

In a round-bottom flask, 7.58 g of propane-1,3-diamine, 16.37 g of trimethyl orthoacetate and 0.60 g of lanthanum (III) trifluoromethanesulfonate were mixed and the mixture was heated to 100° C. while stirring for 24 hours. Thereafter, the reaction mixture was freed of the volatile constituents under reduced pressure.

This gave 5.97 g of a white solid.

$^1$H NMR (CDCl$_3$): δ 1.75 (quint, 2H, J=5.8, NCH$_2$CH$_2$CH$_2$N), 1.83 (s, 3H, CH$_3$), 3.30 (t, 4H, J=5.8, NCH$_2$).

FT-IR: 3214, 3177, 2996, 2925, 2843, 1630, 1542, 1475, 1438, 1380, 1360, 1322, 1294, 1273, 1204, 1191, 1139, 1114, 1095, 1035, 1009, 977, 915, 875, 839, 731.

Preparation of Amidines of the Formula (I)

Amidine K-1: 1-(2-Hydroxy-3-phenoxyprop-1-yl)-2-methyl-1,4,5,6-tetrahydropyrimidine In a round-bottom flask, 1.26 g of amidine HZ-1 were mixed with 1.93 g of PGE and heated to 80° C. for 3 hours. This gave an odorless, yellow oil of high viscosity.

FT-IR: 3060, 2925, 2852, 2714, 1598, 1586, 1494, 1430, 1379, 1359, 1316, 1299, 1241, 1172, 1153, 1077, 1036, 1020, 951, 918, 881, 814, 751, 690.

Amidine K-2: 1-(2-Hydroxy-3-(3-triethoxysilylpropoxy)prop-1-yl)-2-methyl-1,4,5,6-tetrahydropyrimidine In a round-bottom flask, 1.55 g of amidine HZ-1 were mixed with 4.21 g of GLYEO and heated to 100° C. until, after 3.5 hours, no GLYEO was detectable any longer by means of gas chromatography. This gave an odorless yellow oil. $^1$H NMR (CDCl$_3$): δ 0.62 (br m, 2H, CH$_2$Si), 1.20 (t, 9H, J=6.8, CH$_2$CH$_3$), 1.6-1.75 (m, 2H, CH$_2$CH$_2$Si), 1.77-1.85 (m, 2H, NCH$_2$CH$_2$CH$_2$N), 1.99 (s, 3H, N=CCH$_3$), 3.22-3.3 (m, 6H, CH$_2$N), 3.3-3.5 und 3.65 (m, 4H, CH$_2$OCH$_2$), 3.81 (q, 6H, J=6.9, SiOCH$_2$), 4.16 (br m, 1H, CHOH).

FT-IR: 2971, 2925, 2882, 2863, 1615, 1550, 1482, 1433, 1379, 1318, 1294, 1261, 1194, 1164, 1100, 1074, 1031, 951, 880, 850, 772, 655.

Amidine K-3: tert-Butyl 3-(2-methyl-1,4,5,6-tetrahydropyrimidin-1-yl)propionate

In a round-bottom flask, 2.20 g of amidine HZ-1 were mixed with 2.72 g of TBA and heated to 100° C. until, after 5 hours, no TBA was detectable any longer by means of gas chromatography. Thereafter, the reaction mixture was freed of the volatile constituents under reduced pressure. This gave an odorless yellow oil.

$^1$H NMR (CDCl$_3$): δ 1.47 (s, 9H, C(CH$_3$)$_3$), 1.81 (t, 2H, J=5.8, NCH$_2$CH$_2$CH$_2$N), 1.99 (s, 3H, N=CCH$_3$), 2.44 (t, 2H, J=7.3, CH$_2$C=O), 3.17 (t, 2H, J=5.9, NCH$_2$$^{Cy}$), 3.27-3.32 (m, 2H, NCH$_2$$^{Cy}$), 3.45 (t, 2H, J=7.2, NCH$_2$CH$_2$C=O).

FT-IR: 3220, 2974, 2929, 2848, 1723, 1669, 1618, 1551, 1422, 1366, 1316, 1281, 1253, 1211, 1150, 1119, 1083, 1046, 1008, 988, 953, 922, 882, 845, 753, 695.

Amidine K-4: Tetrahydrofurfuryl 3-(2-methyl-1,4,5,6-tetrahydropyrimidin-1-yl)-2-methylpropionate In a round-bottom flask, 2.03 g of amidine HZ-1 were mixed with 3.36 g of THFMA and heated to 100° C. until, after 5 hours, no THFMA was detectable any longer by means of gas chromatography. Thereafter, the reaction mixture was freed of the volatile constituents under reduced pressure. This gave an odorless orange oil.

FT-IR: 3292, 2930, 2860, 1732, 1696, 1638, 1615, 1564, 1496, 1440, 1377, 1361, 1319, 1287, 1259, 1208, 1173, 1140, 1068, 1031, 986, 952, 919, 885, 841, 814, 724, 688.

Amidine K-5: Reaction mixture comprising 1,1,1-trimethylolpropane bis(3-(2-methyl-1 1,4,5,6-tetrahydropyrimidin-1-yl)propionate) acrylate In a round-bottom flask, 2.45 g of amidine HZ-1, 3.56 g of TMPTA and 10 mL of tetrahydrofuran were mixed and heated to 80° C. until, after 24 hours, no TMPTA was detectable any longer by means of gas chromatography.

Thereafter, the reaction mixture was freed of the volatile constituents under reduced pressure. This gave an odorless, yellow oil of high viscosity.

FT-IR: 3258, 2928, 2853, 1729, 2696, 1637, 1613, 1554, 1494, 1443, 1382, 1319, 1284, 1206, 1171, 1119, 1048, 1030, 992, 949, 914, 885, 852, 841, 778, 713, 686.

Amidine K-6: 3-Triethoxysilylpropyl 3-(2-methyl-1,4,5,6-tetrahydropyrimidin-1-yl)-2-methylpropionate In a round-bottom flask, 1.97 g of amidine HZ-1, 5.15 g of Y-9936 and 8 ml of tetrahydrofuran were mixed and heated to 90° C. for 6 hours. Thereafter, the reaction mixture was freed of the volatile constituents under reduced pressure.

This gave an odorless yellow oil.

FT-IR: 3180, 2971, 2927, 2883, 1731, 1720, 1637, 1619, 1566, 1497, 1440, 1383, 1319, 1295, 1254, 1166, 1075, 1018, 951, 886, 841, 765, 690.

Amidine K-7: 3-(2-Methyl-1,4,5,6-tetrahydropyrimidin-1-yl)-1-morpholinopropan-1-one In a round-bottom flask, 1.16 g of amidine HZ-1 and 1.68 g of NAM were mixed and heated to 80° C. for 4 hours. This gave an odorless yellow oil which solidified when left to stand at room temperature.

$^1$H NMR (CDCl$_3$): δ 1.80-1.87 (m, 2H, NCH$_2$CH$_2$CH$_2$N), 2.01 (s, 3H, CH$_3$), 2.53 (t, 2H, J=7.3, CH$_2$C=O), 3.16-3.32 and 3.27-3.34 (2×m, 2×2 H, NCH$_2$CH$_2$CH$_2$N), 3.44-3.5 (m, 2H, CH$_2$N$^{morpholine}$), 3.53 (t, 2H, J=7.5, NCH$_2$CH$_2$C=O), 3.6-3.65 (m, 2H, CH$_2$N$^{morpholine}$), 3.66-3.7 (m, 4H, CH$_2$O).

FT-IR: 3177, 2924, 2851, 1611, 1424, 1380, 1358, 1316, 1298, 1270, 1230, 1214, 1113, 1085, 1068, 1025, 1008, 982, 845, 915, 882, 847, 790, 720.

Amidine K-8: Diethyl 2-(2-methyl-1,4,5,6-tetrahydropyrimidin-1-yl)succinate

In a round-bottom flask, 1.84 g of amidine HZ-1 and 3.28 g of DEM were mixed and heated to 60° C. until, after 1 hour, no DEM was detectable any longer by means of thin-layer chromatography. This gave an odorless orange oil.

FT-IR: 3221, 2979, 2933, 2853, 1729, 1674, 1625, 1568, 1502, 1475, 1442, 1414, 1393, 1361, 1295, 1269, 1156, 1096, 1026, 974, 957, 882, 824, 792, 777, 735, 690.

Preparation of Polyethers Containing Silane Groups

Polymer STP-1

With exclusion of moisture, 1000 g of Acclaim® 12200 polyol (polyoxypropylenediol having a low level of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP) and 0.1 g of bismuth tris(neodecanoate) (10% by weight in DIDP) were heated up to 90° C. while stirring constantly and left at this temperature until the content of free isocyanate groups determined by titrimetry had reached a stable value of 0.63% by weight. Subsequently, 63.0 g of diethyl N-(3-trimethoxysilylpropyl)-aminosuccinate (adduct formed from 3-aminopropyltrimethoxysilane and diethyl maleate; prepared according to the details in U.S. Pat. No. 5,364,955) were mixed in and the mixture was stirred at 90° C. until it was no longer possible to detect any free isocyanate by means of FT-IR spectroscopy. The polyether containing trimethoxysilane groups thus obtained, having a silane equivalent weight of about 6880 g/eq (calculated from the amounts used), was cooled down to room temperature and stored with exclusion of moisture.

Commercial Catalysts Used:

DBU 1,8-diazabicyclo[5.4.0]undec-7-ene (Lupragen® N 700, from BASF)

TMG 1,1,3,3-tetramethylguanidine (from Sigma-Aldrich)

Compositions Based on Polymers Containing Silane Groups:

Comparative examples in tables 1 to 4 are indicated by "(Ref)".

Compositions Z1 to Z10:

A composition composed of 96.5 g of polymer STP-1, 0.5 g of vinyltrimethoxysilane and 3.0 g of 3-aminopropyltrimethoxysilane was blended with various catalysts in the amount specified according to table 1, and the mixture was tested for viscosity and skin time (ST) under standard climatic conditions, before and after storage. The skin time serves as a measure of the activity of the catalyst in relation to the crosslinking reaction of the silane groups, i.e. of the crosslinking rate; the change in viscosity and the skin time after storage are a measure of storage stability. In addition, the mixture applied, after 24 hours under standard climatic conditions, was tested as to whether the surface was dry as desired or whether a greasy film had formed, which is a sign of the exudation of the catalyst owing to poor compatibility with the cured polymer, and/or whether the surface was tacky, which is a sign of incomplete curing. In addition, the mixture was used to produce a film of thickness 2 mm, which was left to cure under standard climatic conditions for 7 days and tested for mechanical properties. The results are shown in tables 1 and 2. "Comp." stands for "composition".

TABLE 1

| Comp. | Catalyst | Amount | Concentration[1] | Viscosity [Pa · s] fresh | Viscosity [Pa · s] stored[2] | Viscosity [Pa · s] increase | ST fresh | ST stored[2] |
|---|---|---|---|---|---|---|---|---|
| Z1 | Amidine K-1[3] | 0.46 g | 1.9 | 29.2 | 30.5 | 4% | 20' | 24' |
| Z2 | Amidine K-2 | 0.69 g | 1.9 | 22.0 | 28.3 | 29% | 27' | 29' |
| Z3 | Amidine K-3 | 0.41 g | 1.9 | 21.3 | 25.5 | 20% | 29' | 32' |
| Z4 | Amidine K-4 | 0.49 g | 1.9 | 21.9 | 29.1 | 33% | 30' | 42' |
| Z5 | Amidine K-5 | 0.48 g | 1.9 | 30.6 | 35.4 | 16% | 53' | 54' |
| Z6 | Amidine K-6 | 0.71 g | 1.9 | 29.3 | 32.1 | 10% | 28' | 29' |
| Z7 | Amidine K-7[3] | 0.44 g | 1.9 | 30.0 | 38.0 | 27% | 25' | 21' |
| Z8 | Amidine K-8 | 0.50 g | 1.9 | 30.3 | 34.5 | 14% | 29' | 30' |
| Z9 (ref.) | DBU | 0.28 g | 1.9 | 27.2 | 36.9 | 36% | 25' | 29' |
| Z10 (ref.) | TMG | 0.21 g | 1.9 | 22.3 | 24.6 | 10% | 65' | 75' |

[1]mmol of amidine or guanidine groups per 100 g of polyether containing silane groups.
[2]for 7 days at 60° C. in a closed container.
[3]as a solution (30% by wt.) in N-ethylpyrrolidone.

TABLE 2

| Comp. | Surface after 24 h | Tensile strength | Elongation at break | Modulus of elasticity 0-5% | Modulus of elasticity 0-50% |
|---|---|---|---|---|---|
| Z1 | dry | 0.67 MPa | 89% | 1.29 MPa | 0.82 MPa |
| Z2 | almost dry | 0.71 MPa | 100% | 1.23 MPa | 0.82 MPa |
| Z3 | almost dry | 0.68 MPa | 95% | 1.25 MPa | 0.80 MPa |
| Z4 | almost dry | 0.73 MPa | 110% | 1.25 MPa | 0.79 MPa |
| Z5 | dry | 0.78 MPa | 126% | 1.21 MPa | 0.79 MPa |
| Z6 | dry | 0.82 MPa | 99% | 1.26 MPa | 0.83 MPa |
| Z7 | dry | 0.69 MPa | 88% | 1.22 MPa | 0.81 MPa |
| Z8 | dry | 0.70 MPa | 95% | 1.17 MPa | 0.82 MPa |
| Z9 (ref.) | greasy | 0.58 MPa | 72% | 1.16 MPa | 0.77 MPa |
| Z10 (ref.) | tacky | 0.62 MPa | 90% | 1.19 MPa | 0.75 MPa |

Compositions Z11 and Z12

In a round-bottom flask, 71.1 g of an OH-terminated linear polydimethylsiloxane having a viscosity of about 50,000 mPas at 23° C. (Wacker® Silicone Rubber Polymer FD 50, from Wacker) were blended with 2.6 g of vinyltris(methylethylketoximo)silane and mixed under reduced pressure for 15 minutes. 26.3 g of trimethylsilyl-terminated polydimethylsiloxane (Wacker® AK 100 silicone oil, from Wacker) were stirred into the polydimethylsiloxane having vinylbis(methylethylketoximo)silyl end groups that was obtained in this way. This mixture was blended with various catalysts according to table 3 below and, as described for composition Z1, tested for viscosity, skin time (ST), surface characteristics and mechanical properties. The results are shown in tables 3 and 4. "Comp." stands for "composition".

TABLE 3

| Comp. | Catalyst | Amount | Concentration[1] | Viscosity [Pa · s] | | | ST | |
|---|---|---|---|---|---|---|---|---|
| | | | | fresh | stored[2] | increase | fresh | stored[2] |
| Z11 | Amidine K-2 | 0.15 g | 0.6 | 13.1 | 9.6 | −27% | 23' | 27' |
| Z12 (ref.) | DBU | 0.06 g | 0.6 | 13.0 | 10.2 | −22% | 13' | 14' |

[1]mmol of amidine groups per 100 g of ketoximato-polydimethylsiloxane polymer.
[2]for 7 days at 70° C. in a closed container.

TABLE 4

| Comp. | Surface after 24 h | Tensile strength | Elongation at break | Modulus of elasticity | |
|---|---|---|---|---|---|
| | | | | 0-5% | 0-50% |
| Z11 | dry | 0.18 MPa | 240% | 0.20 MPa | 0.11 MPa |
| Z12 (ref.) | almost dry | 0.25 MPa | 289% | 0.22 MPa | 0.16 MPa |

The invention claimed is:

1. An amidine of the formula (I)

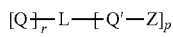   (I)

wherein p is 1 and r is 0,

L is a monovalent hydrocarbyl radical having 1 to 6 carbon atoms and containing an alkoxysilane group, Q is a glycidoxy group, Q' is a divalent connecting unit formed from the reaction of a reactive Q group with HZ, and Z is an aliphatic amidine group bonded via a nitrogen atom.

2. An amidine as claimed in claim 1, wherein Q' is

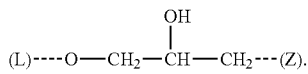

3. An amidine as claimed in claim 1, wherein said amidine is of formula (I'):

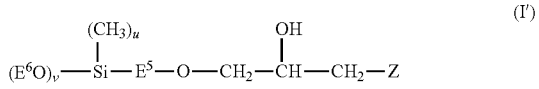   (I')

wherein

E⁵ is an alkylene radical having 1 to 6 carbon atoms,

E⁶ is an alkyl radical having 1 to 4 carbon atoms, u is 0 or 1, and v is 2 or 3, with the proviso that (u+v) equals 3, and Z is an aliphatic amidine group bonded via a nitrogen atom.

4. An amidine as claimed in claim 1, wherein L is triethoxysilylpropyl or trimethoxysilylpropyl.

5. An amidine as claimed in claim 1, wherein Z is

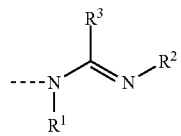

wherein $R^1$ is a hydrogen radical or an alkyl or cycloalkyl or aralkyl radical having 1 to 8 carbon atoms or together with $R^2$ is $R^4$, $R^2$ is a hydrogen radical or an alkyl, cycloalkyl or aralkyl radical which has 1 to 18 carbon atoms and optionally contains ether oxygen or tertiary amine nitrogen, or together with $R^1$ is $R^4$, $R^3$ is a hydrogen radical or an alkyl or cycloalkyl or aralkyl radical having 1 to 12 carbon atoms, wherein $R^4$ is an optionally substituted 1,2-ethylene, 1,3-propylene or 1,4-butylene radical having 2 to 12 carbon atoms, and wherein $R^2$ and $R^3$ together may also be an alkylene radical having 3 to 6 carbon atoms.

6. An amidine as claimed in claim 5 wherein $R^1$ and $R^2$ together are $R^4$.

7. A process for preparing the amidine of the formula (I) as claimed in claim 1, wherein at least one amidine of the formula HZ is reacted with at least one functional compound of the formula $L-[Q]_{(p+r)}$ wherein p is 1 and r is 0, L is a monovalent hydrocarbyl radical having 1 to 6 carbon atoms and containing an alkoxysilane group, and Q is a glycidoxy group.

8. The process as claimed in claim 7, wherein the amidine of the formula HZ has the formula

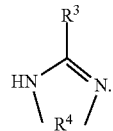

wherein $R^3$ is a hydrogen radical or an alkyl or cycloalkyl or aralkyl radical having 1 to 12 carbon atoms, and $R^4$ is an optionally substituted 1,2-ethylene, 1,3-propylene or 1,4-butylene radical having 2 to 12 carbon atoms.

9. A method comprising applying as catalyst for the crosslinking of a curable composition the amidine of the formula (I) as claimed in claim 1.

10. A method as claimed in claim 9, wherein the curable composition is an epoxy resin composition or a polyurethane composition or an epoxy resin/polyurethane composition or a cyanate ester resin composition or a composition containing silane groups.

11. A method as claimed claim 10, wherein the curable composition is a composition based on polymers containing silane groups selected from the group consisting of polyorganosiloxanes having terminal silane groups and organic polymers containing silane groups.

12. A method as claimed in claim 9, wherein the curable composition is a polyurethane composition or a composition containing silane groups.

13. A curable composition comprising at least one amidine of the formula (I) as claimed in claim 1.

14. The composition as claimed in claim 13, wherein it further comprises at least one polymer containing silane groups.

15. The composition as claimed in claim 13, wherein it is an adhesive or a sealant or a coating.

* * * * *